(12) United States Patent
Dorsch et al.

(10) Patent No.: US 7,579,346 B2
(45) Date of Patent: Aug. 25, 2009

(54) CARBOXAMIDES

(75) Inventors: Dieter Dorsch, Ober-Ramstadt (DE); Bertram Cezanne, Mörfelden-Walldorf (DE); Werner Mederski, Zwingenberg (DE); Christos Tsaklakidis, Weinheim (DE); Hanns Wurziger, Darmstadt (DE); Johannes Gleitz, Darmstadt (DE); Christoph van Amsterdam, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 473 days.

(21) Appl. No.: 10/535,246

(22) PCT Filed: Oct. 30, 2003

(86) PCT No.: PCT/EP03/12080

§ 371 (c)(1), (2), (4) Date: May 18, 2005

(87) PCT Pub. No.: WO2004/046138

PCT Pub. Date: Jun. 3, 2004

(65) Prior Publication Data

US 2006/0052376 A1    Mar. 9, 2006

(30) Foreign Application Priority Data

Nov. 21, 2002  (DE) ................. 102 54 336

(51) Int. Cl.
| | |
|---|---|
| A61K 31/535 | (2006.01) |
| A61K 31/497 | (2006.01) |
| A61K 31/415 | (2006.01) |
| C07D 413/00 | (2006.01) |
| C07D 409/00 | (2006.01) |
| C07D 231/00 | (2006.01) |
| C07D 333/36 | (2006.01) |

(52) U.S. Cl. .............. 514/231.5; 514/252.13; 514/406; 544/146; 546/213; 548/365.7; 549/60; 549/69

(58) Field of Classification Search ................. 544/146; 546/213; 548/365.7; 549/60, 69; 514/231.5, 514/252.13, 406
See application file for complete search history.

(56) References Cited

U.S. PATENT DOCUMENTS

| | | | |
|---|---|---|---|
| 6,638,980 B1 | 10/2003 | Su et al. | |
| 6,906,063 B2 * | 6/2005 | Scarborough et al. | .... 514/222.8 |
| 2003/0176465 A1 | 9/2003 | Mederski et al. | |
| 2004/0038858 A1 | 2/2004 | Dorsch et al. | |

FOREIGN PATENT DOCUMENTS

| | | |
|---|---|---|
| WO | WO0206269 | 1/2002 |
| WO | WO0248099 | 6/2002 |
| WO | WO02057236 | 7/2002 |
| WO | WO0071510 | 11/2005 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*

* cited by examiner

*Primary Examiner*—Kamal A Saeed
*Assistant Examiner*—Samantha L Shterengarts
(74) *Attorney, Agent, or Firm*—Millen, White, Zelano & Branigan, P.C.

(57) ABSTRACT

Novel compounds of the formula (I), in which D, W, X, Y, T, m and $R^1$ have the meaning indicated in Patent claim 1, are inhibitors of coagulation factor Xa and can be employed for the prophylaxis and/or therapy of thromboembolic diseases and for the treatment of tumours.

25 Claims, No Drawings

CARBOXAMIDES

The invention relates to compounds of the formula I

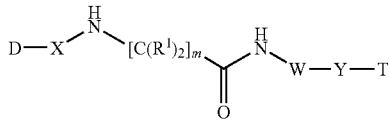

in which
D denotes aromatic carbo- or heterocycle having 0 to 4 N, O and/or S atoms which is unsubstituted or mono- or polysubstituted by Hal, A, $OR^2$, $N(R^2)_2$, $NO_2$, CN, $COOR^2$ or $CON(R^2)_2$,
X denotes —C=O or $C(R^3)_2$,
W denotes $-[C(R^3)_2]_n-$,
$R^1$ denotes H or A, which may be substituted by $OR^3$, $S(O)_nR^3$, $N(R^3)_2$, CN, $COOR^3$, $CON(R^3)_2$, $OCON(R^3)_2$, $N(R^3)COOR^3$, $N(R^3)CON(R^3)_2$, $N(R^3)SO_2R^3$, $SO_2N(R^3)_2$ or —C≡C—,
$R^2$ denotes H, A, $-[C(R^3)_2]_n$—Ar', $-[C(R^3)_2]_n$-Het', $-[C(R^3)_2]_n$-cycloalkyl, $-[C(R^3)_2]_n-N(R^3)_2$ or $-[C(R^3)_2]_n-OR^3$,
$R^3$ denotes H or A,
Y denotes alkylene, cycloalkylene, Het-diyl or Ar-diyl,
T denotes a mono- or bicyclic saturated, unsaturated or aromatic carbo- or heterocycle having 0 to 4 N, O and/or S atoms which is mono- or disubstituted by =O, =S, $=NR^2$, =N—CN, =N—$NO_2$, $=NOR^2$, $=NCOR^2$, $=NCOOR^2$, $=NOCOR^2$ and may furthermore be mono-, di- or trisubstituted by $R^2$, Hal, A, $-[C(R^3)_2]_n$—Ar, $-[C(R^3)_2]_n$-Het, $-[C(R^3)_2]_n$-cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_nA$,
A denotes unbranched or branched alkyl having 1-10 C atoms, in which one or two $CH_2$ groups may be replaced by O or S atoms and/or by —CH=CH— groups and/or also 1-7H atoms may be replaced by F,
Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2N(R^2)_2$, $S(O)_nA$, $[C(R^3)_2]_n$—$COOR^2$ or —O—$[C(R^3)_2]_o$—$COOR^2$,
Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_nA$, $-[C(R^3)_2]_n$—$COOR^3$ or —O—$[C(R^3)_2]_o$—$COOR^3$,
Het denotes a mono- or bicyclic saturated, unsaturated or aromatic heterocycle having 1 to 4 N, O and/or S atoms, which may be unsubstituted or mono-, di- or trisubstituted by carbonyl oxygen, =S, $=N(R^2)_2$, Hal, A, $-[C(R^3)_2]_n$—Ar, $-[C(R^3)_2]_n$-Het', $-[C(R^3)_2]_n$-cycloalkyl, $-[C(R^3)_2]_n$—$OR^2$, $-[C(R^3)_2]_n$—$N(R^3)_2$, $NO_2$, CN, $-[C(R^3)_2]_n$—$COOR^{2'}$ $-[C(R^3)_2]_n$—$CON(R^2)_2$, $-[C(R^3)_2]_n$—$NR^2COA$, $NR^2CON(R^2)_2$, $-[C(R^3)_2]_n$—$NR^2SO_2A$, $COR^2$, $SO_2NR^2$ and/or $S(O)_nA$,
Het' denotes a mono- or bicyclic saturated, unsaturated or aromatic heterocycle having 1 to 4 N, O and/or S atoms, which may be unsubstituted or mono- or disubstituted by carbonyl oxygen, =S, $=N(R^3)_2$, Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2NR^3$ and/or $S(O)_nA$,
Hal denotes F, Cl, Br or I,
m denotes 1 or 2,
n denotes 0, 1 or 2,
o denotes 1, 2 or 3,
and pharmaceutically usable derivatives, solvates and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexy, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 or WO 00/71516. Cyclic guanidines for the treatment of thromboembolic diseases are described, for example, in WO 97/08165. Aromatic heterocyces having a factor Xa inhibitory activity are disclosed, for example, in WO 96/10022. Substituted N-[(aminoiminomethyl)phenylalkyl]azaheterocyclylamides as factor Xa inhibitors are described in WO 96/40679.

Other carboxamide derivatives are disclosed in WO 02/48099 and WO 02/57236.

Further factor Xa inhibitors are described in WO 00/76970, WO 00/76971 and WO 01/96303.

The antithrombotic and anticoagulant effect of the compounds according to the invention is attributed to the inhibitory action against activated coagulation protease, known by the name factor Xa, or to the inhibition of other activated serine proteases, such as factor VI la, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin.

The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation Cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoural action of TF-VII and factor Xa inhibitors for various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease.

The compounds are also employed in combination with other thrombolytic agents in myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in patients in vivo, or as anticoagulants for the preservation of blood, plasma and other blood products in vitro. The compounds according to the invention are furthermore used for diseases in which blood coagulation makes a crucial contribution towards the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 4547).

In the treatment of the diseases described, the compounds according to the invention are also employed in combination with other thrombolytically active compounds, such as, for example, with the "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the thrombus formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to Claims 1-16 and pharmaceutically usable derivatives, solvates and stereoisomers thereof, characterised in that a) a compound of the formula II

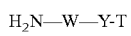

in which

W, Y and T have the meanings indicated in Claim 1, is reacted with a compound of the formula III

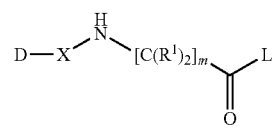

in which

L denotes Cl, Br, I or a free or reactively functionally modified OH group, and $R^1$, m, X and D have the meanings indicated in Claim 1, or b) for the preparation of compounds of the formula I in which X denotes —C=O, a compound of the formula IV

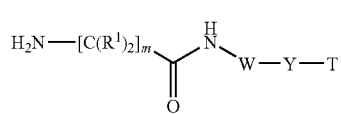

in which $R^1$, m, W, Y and T have the meanings indicated in Claim 1, is reacted with a compound of the formula V

in which

L denotes Cl, Br, I or a free or reactively functionally modified OH group, and

D has the meaning indicated in Claim 1, or c) for the preparation of compounds of the formula I in which X denotes CH$_2$, a compound of the formula IV

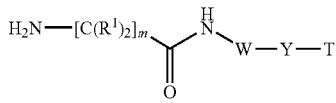

in which R$^1$, m, W, Y and T have the meanings indicated in Claim 1, is reacted with a compound of the formula VI

D-CHO                                                     VI in which

D has the meaning indicated in Claim 1, in a reductive amination, and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds. For all radicals which occur more than once, such as, for example, R$^1$ in (R$^1$)$_2$, their meanings are independent of one another.

Above and below, the radicals and parameters D, W, X, Y, T, R$^1$ have the meanings indicated in the case of the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, in which one or two CH$_2$ groups may be replaced by O or S atoms and/or by —CH=CH— groups and/or also 1-7H atoms may be replaced by F.

Cycloalkyl preferably denotes cyclopropyl, cyclobutyl, cyclopentyl, cyclohexyl or cycloheptyl.

Alkylene preferably denotes methylene, ethylene, propylene, butylene, pentylene or hexylene, furthermore branched alkylene.

COR$^2$ denotes, for example, CHO or —COA.

—COA (acyl) preferably denotes acetyl, propionyl, furthermore also butyryl, pentanoyl, hexanoyl or, for example, benzoyl.

Hal preferably denotes F, Cl or Br, but also I.

Aromatic carbocycle denotes, for example, phenyl, biphenyl or naphthyl.

Saturated carbocycle preferably denotes cycloalkyl, such as, for example, cyclohexane or cyclopentane.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-trichlorophenyl, 2,4,6-trimethoxyphenyl, 2-hydroxy-3,5-dichlorophenyl, p-iodophenyl, 3,6-di-chloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono- or disubstituted by Hal, A, OA, SO$_2$A, COOR$^2$, SO$_2$NH$_2$ or CN. Ar particularly preferably denotes, for example, phenyl which is unsubstituted or mono- or disubstituted by Hal, A, OA, SO$_2$A, SO$_2$NH$_2$, COOR$^2$ or CN, such as, for example, phenyl, 2-methylsulfonylphenyl, 2-aminosulfonylphenyl, 2-, 3- or 4-chlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl or 4-ethoxycarbonylphenyl.

Ar very particularly preferably denotes phenyl which is unsubstituted or mono- or disubstituted by A and/or Hal.

Y preferably denotes Het-diyl or Ar-diyl, particularly preferably 1,4-phenylene which is unsubstituted or monosubstituted by A, OA, Cl or F, furthermore also pyridinediyl, preferably pyridine-2,5-diyl, or piperidinediyl.

In particular, Y denotes 1,3- or 1,4-phenylene, which is unsubstituted or monosubstituted by methyl, ethyl, propyl, Cl or F.

Y very particularly preferably denotes phenylene which is unsubstituted or mono- or disubstituted by A and/or Hal, for example 1,4-phenylene which is unsubstituted or monosubstituted by methyl, ethyl, propyl, Cl or F.

Unsubstituted Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, 4- or 5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, 4- or -5-pyrrolyl, 1-, 2- or 3-pyrrolidinyl, tetrahydro-1-, -2- or 4-imidazolyl, 2,3-dihydro-1-, -2-, -3-, 4- or -5-pyrazolyl, tetrahydro-1-, -3- or 4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, 4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, 4-, -5-, -6-, -7- or -8-isoquinolyl, 2-, 3-, 5-, 6-, 7- or 8-3,4-dihydro-2H-benzo-1,4-oxazinyl, Furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxo-methylenedioxy) phenyl or alternatively 3,4-dihydro-2H-1,5-benzodioxepin-6- or -7-yl, furthermore preferably 2,3-dihydrobenzofuranyl or 2,3-dihydro-2-oxofuranyl.

Unsubstituted Het' has the preferred meanings indicated above for Het.

T preferably denotes a mono- or bicyclic saturated, unsaturated or Aromatic heterocycle having 1 to 2 N and/or O atoms, which is mono- or disubstituted by =O, =S, =NR$^2$, =N—CN, =N—NO$_2$, =NOR$^2$, =NCOR$^2$, =NCOOR or =NOCOR$^2$ and may furthermore be mono- or disubstituted by Hal or A.

In a further embodiment, T preferably denotes, for example, 2-iminopiperidin-1-yl, 2-iminopyrrolidin-1-yl, 2-imino-1H-pyridin-1-yl, 3-iminomorpholin-4-yl, 4-imino-1H-pyridin-1-yl, 2,6-diiminopiperidin-1-yl, 2-iminopiperazin-1-yl, 2,6-diiminopiperazin-1-yl, 2,5-diiminopyrrolidin-1-yl, 2-imino-1,3-oxazolidin-3-yl, 3-imino-2H-pyridazin-2-yl, 2-iminoazepan-1-yl, 2-hydroxy-6-iminopiperazin-1-yl or 2-methoxy-6-iminopiperazin-1-yl.

In particular, T denotes a mono- or bicyclic saturated or unsaturated heterocycle having 1 to 2 N and/or O atoms which is mono- or disubstituted by =O, =S or =NH.

T particularly preferably denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo[2.2.2]octan-2-yl, each of which is mono- or disubstituted by =O or =NH, D preferably denotes aromatic five-ring heterocycle having 1 to 2 N, O and/or S atoms which is unsubstituted or mono- or disubstituted by Hal. In a further embodiment, D preferably denotes thienyl, thiazolyl or furyl, each of which is mono- or disubstituted by Hal.

D furthermore preferably denotes thienyl or phenyl, each of which is mono- or disubstituted by Hal.

In particular, D denotes a thienyl ring which is mono- or disubstituted by Hal.

R$^1$ preferably denotes H or A, which may be substituted by OR$^3$, CON(R$^3$)$_2$, N(R$^3$)$_2$, S(O)$_n$R$^3$, COOR$^3$, OCON(R$^3$)$_2$, N(R$^3$)COOR$^3$ or —C≡C—.

In particular, R$^1$ denotes H or A, which may be substituted by OH, OA', CONH$_2$, NH$_2$, N(A')$_2$, SO$_2$A', SA', COOA', COOH, OCONH$_2$, —C≡C— or NHCOOA', where A' denotes alkyl having 1, 2, 3, 4, 5 or 6 C atoms.

R$^2$ preferably denotes, for example, H or alkyl having 1, 2, 3, 4, 5 or 6 C atoms.

R$^3$ preferably denotes H or alkyl having 1, 2, 3, 4, 5 or 6 C atoms.

X preferably denotes —C=O or CH$_2$, very particularly preferably —C=O.

W is preferably a bond, i.e. it is absent or W is CH$_2$. W is very particularly preferably absent.

The compounds of the formula I can have one or more centres of chirality and therefore occur in various stereoisomeric forms. The formula I covers all these forms.

Accordingly, the invention relates, in particular, to the compounds of the formula I in which at least one of the said radicals has one of the preferred meanings indicated above. Some preferred groups of compounds can be expressed by the following sub-formulae Ia to Io, which conform to the formula I and in which the radicals not designated in greater detail have the meaning indicated in the case of the formula 1, but in which in Ia D denotes aromatic five-ring heterocycle having 1 to 2 N, O and/or S atoms which is unsubstituted or mono- or disubstituted by Hal;

in Ib D denotes a thienyl ring which is mono- or disubstituted by Hal;

in Ic R$^2$ denotes H or alkyl having 1, 2, 3, 4, 5 or 6 C atoms;

in Id R$^1$ denotes H or A, which may be substituted by OR$^3$, CON(R$^3$)$_2$, N(R$^3$)$_2$, S(O)NR$^3$, COOR$^3$, OCON(R$^3$)$_2$, N(R$^3$)COOR$^3$ or —C≡C—;

in Ie X denotes —C=O;

in If W is absent;

in Ig Y denotes Ar-diyl;

in Ih T denotes a mono- or bicyclic saturated, unsaturated or aromatic heterocycle having 1 to 2 N and/or O atoms which is mono- or disubstituted by =O, =S, =NR$^2$, =N—CN, =N—NO$_2$, =NOR$^2$, =NCOR$^2$, =NCOOR$^2$ or =NOCOR$^2$ and may Furthermore be mono- or disubstituted by Hal or A;

in Ii T denotes a mono- or bicyclic saturated or unsaturated heterocycle having 1 to 2 N and/or O atoms which is mono- or disubstituted by =O, =S or =NH;

in Ij T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo[2.2.2]octan-2-yl, each of which is mono- or disubstituted by =O or =NH;

in lk Ar denotes phenyl which is unsubstituted or mono- or disubstituted by Hal, A, OA, $SO_2A$, $COOR^2$, $SO_2NH_2$ or CN;

in ll Ar denotes phenyl which is unsubstituted or mono- or disubstituted by A and/or Hal;

in lm D denotes aromatic five-ring heterocycle having 1 to 2 N, O and/or S atoms which is unsubstituted or mono- or disubstituted by Hal, $R^1$ denotes H or A, which may be substituted by $OR^3$, $CON(R^3)_2$, $N(R^3)_2$, $S(O)_n$, $R^3$, $COOR^3$, $OCON(R^3)_2$, $N(R^3)COOR^3$ or —C≡C—, $R^2$ denotes H or alkyl having 1, 2, 3, 4, 5 or 6 C atoms, X denotes —C=O or $CH_2$, W is absent, Y denotes Ar-diyl, Ar denotes phenyl which is unsubstituted or mono- or disubstituted by A and/or Hal, T denotes a mono- or bicyclic saturated or unsaturated heterocycle having 1 to 2 N and/or O atoms which is mono- or disubstituted by =O, =S or =NH;

in ln D denotes thienyl, thiazolyl or furyl, each of which is mono- or disubstituted by Hal, $R^1$ denotes H or A, which may be substituted by $OR^3$, $CON(R^3)_2$, $N(R^3)_2$, $S(O)NR^3$, $COOR^3$, $OCON(R^3)_2$, $N(R^3)COOR^3$ or —C≡C—, $R^2$ denotes H or alkyl having 1, 2, 3, 4, 5 or 6 C atoms, X denotes —C=O or $CH_2$, W is absent, Y denotes Ar-diyl, Ar denotes phenyl which is unsubstituted or mono- or disubstituted by A and/or Hal, T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo[2.2.2]octan-2-yl, each of which is mono- or disubstituted by =O or =NH;

in lo D denotes thienyl or phenyl, each of which is mono- or disubstituted by Hal, $R^1$ denotes H or alkyl having 1-6 C atoms, which may be substituted by $OR^3$, $CON(R^3)_2$, $N(R^3)_2$, $S(O)_nR^3$, $COOR^3$, $OCON(R^3)_2$, $N(R^3)COOR^3$ or —C≡C—, $R^2$ denotes H or alkyl having 1, 2, 3, 4, 5 or 6 C atoms, $R^3$ denotes H or alkyl having 1, 2, 3, 4, 5 or 6 C atoms, X denotes —C=O or $CH_2$, W is absent or denotes $CH_2$, Y denotes Ar-diyl, A denotes alkyl having 1, 2, 3, 4, 5 or 6 C atoms, in which one or two $CH_2$ groups may be replaced by O or S atoms and/or by —CH=CH— groups and/or also 1-7H atoms may be replaced by F, Ar denotes phenyl which is unsubstituted or mono- or disubstituted by A and/or Hal, T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo[2.2.2]octan-2-yl, each of which is mono- or disubstituted by =O or =NH;

and pharmaceutically usable derivatives, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ, so that they are not isolated from the reaction mixture, but instead are immediately converted further into the compounds of the formula I.

The starting compounds of the formulae II, III, IV and V are generally known. If they are novel, they can, however, be prepared by methods known per se.

Compounds of the formula I can preferably be obtained by reacting compounds of the formula II with compounds of the formula III.

In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;).

Activated esters are advantageously formed in situ, for example by addition of HOBt or N-hydroxysuccinimide.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula III.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents.

Compounds of the formula I in which X denotes —C=O can furthermore preferably be obtained by reacting compounds of the formula IV with compounds of the formula V.

The reaction is generally carried out in an inert solvent and under conditions as indicated above.

In the compounds of the formula V, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Activated esters are advantageously formed in situ, for example by addition of HOBt or N-hydroxysuccinimide.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula V.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Suitable inert solvents are those mentioned above.

Compounds of the formula I in which X denotes $CH_2$ can furthermore preferably be obtained by reacting compounds of the formula IV with compounds of the formula VI.

The reaction is generally carried out under conditions of a reductive amination, as are known to any person skilled in the art.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

These compositions can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The compositions indicated may be sterilised and/or comprise adjuvants, such as lubricants, preservatives, stabilisers and/or wetting agents, emulsifying agents, salts for modifying the osmotic pressure, buffer substances, colorants, flavours and/or a plurality of further active ingredients, for example one or more vitamins.

The compounds of the formula I and physiologically acceptable salts thereof can be used for combating and preventing thromboembolic diseases, such as thrombosis, myocardial infarction, arteriosclerosis, inflammation, apoplexy, angina pectoris, restenosis after angioplasty, claudicatio intermittens, migraine, tumours, tumour diseases and/or tumour metastases.

In general, the substances according to the invention are preferably administered here in doses between about 1 and 500 mg, in particular between 5 and 100 mg, per dosage unit. The daily dose is preferably between about 0.02 and 10 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases, in combination with at least one further medicament active ingredient.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):
EI (electron impact ionisation) M+
FAB (fast atom bombardment) (M+H)+
ESI (electrospray ionisation) (M+H)+ (unless stated otherwise)

EXAMPLE 1

The preparation of (R)-2-[(5-chlorothiophene-2-carbonyl)amino]-N-[3-methyl-4-(3-oxomorpholin-4-yl)phenyl]4-methylvaleramide is carried out analogously to the following scheme:

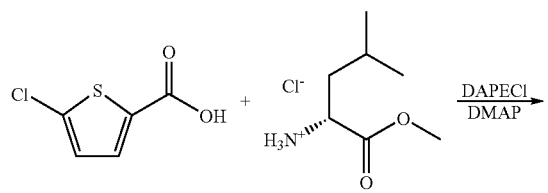

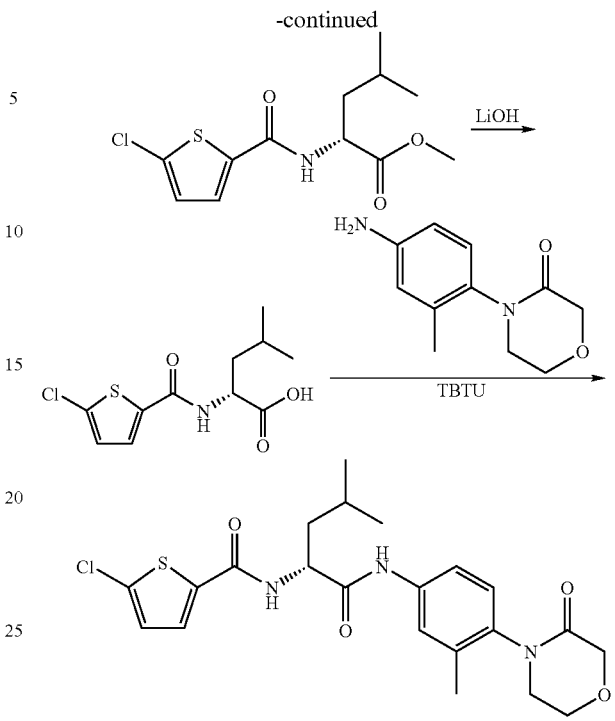

5.50 g (45.0 mmol) of 4-dimethylaminopyridine (DMAP) and 5.75 g (30.0 mmol) of N-(3-dimethylaminopropyl)-N'-ethylcarbodiimide hydrochloride (DAPECI) are added to a solution of 4.48 g (72.5 mmol) of 2-chlorothiophene-5-carboxylic acid and 5.00 g (27.5 mmol) of D-leucine methyl ester hydrochloride in 100 ml of acetonitrile, and the mixture is stirred at room temperature for 18 hours. The reaction mixture is evaporated, and the residue is partitioned between tert-butyl methyl ether and water. The organic phase is washed with potassium hydrogensulfate solution, saturated sodium hydrogencarbonate solution and water. The organic phase is dried over sodium sulfate and evaporated: methyl (R)-2-[(5-chlorothiophene-2-carbonyl)amino]4-methylpentanoate as colourless oil; ESI 290.

A solution of 1.20 g (24.0 mmol) of lithium hydroxide in 60 ml of water is added to a solution of 7.00 g (24.25 mmol) of methyl (R)-2-[(5-chlorothiophene-2-carbonyl)amino]4-methylpentanoate in 60 ml of THF, and the mixture is stirred at room temperature for 18 hours. The reaction mixture is evaporated, and the residue is taken up in 25 ml of water. A pH of 3 is set by addition of conc. hydrochloric acid. The precipitate formed is filtered off, washed with water and dried: (R)-2-[(5-chlorothiophene-2-carbonyl)amino]-4-methylpentanoic acid as colourless solid; ESI 276.

202 mg (0.629 mmol) of 2-(1H-benzotriazol-1-yl)-1,1,3,3-tetramethyluronium tetrafluoroborate (TBTU) are added to a solution of 137 mg (0.500 mmol) of (R)-2-[(5-chlorothiophene-2-carbonyl)amino]4-methylpentanoic acid and 103 mg (0.500 mmol) of 4-(4-amino-2-methylphenyl)morpholin-3-one in 1 ml of dimethylformamide (DMF), and the mixture is stirred at room temperature for 18 hours. Saturated aqueous sodium hydrogencarbonate solution is added to the reaction mixture, and the precipitate formed is filtered off, washed with water and dried: (R)-2-[(5-chlorothiophene-2-carbonyl)amino]-N-[3-methyl-4-(3-oxomorpholin-4-yl)phenyl]-4-methylvaleramide ("1A") as colourless solid; ESI 464.

The following compounds are obtained analogously
(S)-2-[(5-chlorothiophene-2-carbonyl)amino]-N-[4-(3-oxomorpholin-4-yl)phenyl]-4-methylvaleramide, ESI 450;
(S)-2-[(5-chlorothiophene-2-carbonyl)amino]-N-[3-methyl-4-(3-oxomorpholin-4-yl)phenyl]-4-methylvaleramide, ESI 464;
(S)-2-[(5-chlorothiophene-2-carbonyl)amino]-N-[4-(2-oxo-2H-pyrazin-1-yl)phenyl]4-methylvaleramide, ESI 445;
(R)-2-[(5-chlorothiophene-2-carbonyl)amino]-N-[4-(3-oxomorpholin-4-yl)phenyl]-4-methylvaleramide, ESI 450;
(R)-2-[(5-chlorothiophene-2-carbonyl)amino]-N-[4-(2-oxo-2H-pyrazin-1-yl)phenyl]4-methylvaleramide ("2A"), ESI 445;
(R)-2-[(5-chlorothiophene-2-carbonyl)amino]-N-[4-(2-oxo-2H-pyridin-1-yl)phenyl]-4-methylvaleramide, ESI 444;
2-[(5-chlorothiophene-2-carbonyl)amino]-N-[3-methyl-4-(2-oxopiperidin-1-yl)phenyl]acetamide,
3-[(5-chlorothiophene-2-carbonyl)amino]-N-[3-methyl-4-(2-oxopiperidin-1-yl)phenyl]propionamide,
(R)-2-[(5-chlorothiophene-2-carbonyl)amino]-N-[3-methyl-4-(3-oxomorpholin-4-yl)phenyl]propionamide, ESI 422;
(R)-2-[(5-chlorothiophene-2-carbonyl)amino]-N-[3-methyl-4-(3-oxomorpholin-4-yl)phenyl]-3-methylbutyramide, ESI 450;
(R)-2-[(5-chlorothiophene-2-carbonyl)amino]-N-[3-methyl-4-(3-oxomorpholin-4-yl)phenyl]butyramide, ESI 436;
(R)-2-[(5-chlorothiophene-2-carbonyl)amino]-N-[3-methyl-4-(3-oxomorpholin-4-yl)phenyl]valeramide, ESI 450;
(R)-2-[(5-chlorothiophene-2-carbonyl)amino]-N-[3-methyl-4-(3-oxomorpholin-4-yl)phenyl]-3-aminocarbonylpropionamide,
2-([(5-chlorothiophene-2-carbonyl)amino]-N-[3-methyl-4-(3-oxomorpholin-4-yl)phenyl]-3-(N,N-dimethylamino)propionamide,
(R)-2-[(5-bromothiophene-2-carbonyl)amino]-N-[4-(3-oxomorpholin-4-yl)phenyl]-4-methylvaleramide, ESI 494, 496;
(R)-2-[(5-chlorothiophene-2-carbonyl)amino]-N-[4-(2-oxopiperidin-1-yl)benzyl]-4-methylvaleramide, ESI 462;
2-[(5-chlorothiophene-2-methyl)amino]-N-[4-(3-oxomorpholin-4-yl)phenyl]-4-methylvaleramide,
(R)-2-[(5-chlorothiophene-2-carbonyl)amino]-N-[4-(3-oxomorpholin-4-yl)phenyl]-3-methylsulfanylpropionamide, ESI 454;
(S)-2-[(5-chlorothiophene-2-carbonyl)amino]-N-[4-(2-oxopiperidin-1-yl)benzyl]-4-methylvaleramide, ESI 462;
(R)-2-[(5-chlorothiophene-2-carbonyl)amino]-N-[4-(3-oxomorpholin-4-yl)phenyl]-3-methylbutyramide, ESI 436;
(R)-2-[(5-chlorothiophene-2-carbonyl)amino]-N-[4-(2-oxo-2H-pyridin-1-yl)phenyl]-3-methylbutyramide, ESI 430;
3-[(5-chlorothiophene-2-carbonyl)amino]-N-[4-(3-oxomorpholin-4-yl)phenyl]propionamide, ESI 408;
3-[(5-chlorothiophene-2-carbonyl)amino]-N-[3-methyl-4-(3-oxomorpholin-4-yl)phenyl]propionamide, ESI 422;
3-[(5-chlorothiophene-2-carbonyl)amino]-N-[4-(2-oxo-2H-pyridin-1-yl)phenyl]propionamide, ESI 402;
2-[(5-chlorothiophene-2-carbonyl)amino]-N-[3-methyl-4-(3-oxomorpholin-4-yl)phenyl]acetamide, ESI 408;
2-[(5-chlorothiophene-2-carbonyl)amino]-N-[4-(3-oxomorpholin-4-yl)phenyl]acetamide, ESI 394;
2-[(5-chlorothiophene-2-carbonyl)amino]-N-[4-(2-oxo-2H-pyridin-1-yl)phenyl]acetamide, ESI 388;
3-[(5-chlorothiophene-2-carbonyl)amino]-N-[4-(2-oxo-2H-pyridin-1-yl)phenyl]-2-butylpropionamide;
(R)-2-[(5-chlorothiophene-2-carbonyl)amino]-N-[4-(3-oxomorpholin-4-yl)phenyl]propionamide, ESI 408;
(R)-2-[(5-chlorothiophene-2-carbonyl)amino]-N-[4-(3-oxomorpholin-4-yl)phenyl]valeramide, ESI 436;
(R)-2-[(5-chlorothiophene-2-carbonyl)amino]-N-[4-(2-oxo-2H-pyridin-1-yl)phenyl]-3-methylsulfanylpropionamide, ESI 448;
(R)-2-[(5-chlorothiophene-2-carbonyl)amino]-N-[4-(2-oxo-2H-pyrazin-1-yl)phenyl]propionamide, ESI 403;
(R)-2-[(5-chlorothiophene-2-carbonyl)amino]-N-[4-(3-oxomorpholin-4-yl)phenyl]4-methylsulfanylbutyramide, ESI 468;
(R)-2-[(5-chlorothiophene-2-carbonyl)amino]-N-[4-(3-oxomorpholin-4-yl)phenyl]butyramide, ESI 422;
(R)-2-[(5-chlorothiophene-2-carbonyl)amino]-N-[4-(3-oxomorpholin-4-yl)phenyl]-3-ethynylpropionamide, ESI 432;
(R)-2-[(5-chlorothiophene-2-carbonyl)amino]-N-[3-methyl-4-(3-oxomorpholin-4-yl)phenyl]-3-ethynylpropionamide, ESI 446;
(R)-2-[(5-chlorothiophene-2-carbonyl)amino]-N-[3-fluoro-4-(3-oxomorpholin-4-yl)phenyl]propionamide, ESI 426;
(R)-2-[(5-chlorothiophene-2-carbonyl)amino]-N-[3-methyl-4-(3-oxomorpholin-4-yl)phenyl]-4-methylsulfanylbutyramide, ESI 482;
(R)-2-[(5-chlorothiophene-2-carbonyl)amino]-N-[4-(3-oxomorpholin-4-yl)phenyl]-3-(tert-butyloxycarbonyl)propionamide, ESI 508;
(R)-2-[(5-chlorothiophene-2-carbonyl)amino]-N-[4-(3-oxomorpholin-4-yl)phenyl]-3-vinylpropionamide, ESI 434;
(R)-2-[(5-chlorothiophene-2-carbonyl)amino]-N-[3-methyl-4-(3-oxomorpholin-4-yl)phenyl]-3-vinylpropionamide, ESI 448;
(R)-2-[(5-chlorothiophene-2-carbonyl)amino]-N-[3-methyl-4-(3-oxomorpholin-4-yl)phenyl]-3-(tert-butyloxycarbonyl)propionamide, ESI 522;
(R)-2-[(5-chlorothiophene-2-carbonyl)amino]-N-[4-(3-oxomorpholin-4-yl)phenyl]4-methoxybutyramide, ESI 452;
(R)-2-[(5-chlorothiophene-2-carbonyl)amino]-N-[3-methyl-4-(3-oxomorpholin-4-yl)phenyl]-4-methoxybutyramide, ESI 466;
(R)-2-[(5-chlorothiophene-2-carbonyl)amino]-N-[3-fluoro-4-(3-oxomorpholin-4-yl)phenyl]-4-methylvaleramide, ESI 468;
(R)-2-[(5-chlorothiophene-2-carbonyl)amino]-N-[3-fluoro-4-(3-oxomorpholin-4-yl)phenyl]valeramide, ESI 454;
(R)-2-[(5-chlorothiophene-2-carbonyl)amino]-N-[3-chloro-4-(3-oxomorpholin-4-yl)phenyl]propionamide, ESI 443;
(R)-2-[(5-chlorothiophene-2-carbonyl)amino]-N-[4-(3-oxomorpholin-4-yl)phenyl]4-(tert-butyloxycarbonyl)butyramide, ESI 467 (M-tert-butyl+H$^+$); 545 (M+Na$^+$);

(R)-2-[(5-chlorothiophene-2-carbonyl)amino]-N-[3-methyl-4-(3-oxomorpholin-4-yl)phenyl]-4-(tert-butyloxycarbonyl)butyramide, ESI 1071 (2 M+H⁺);
(R)-2-[(5-chlorothiophene-2-carbonyl)amino]-N-[4-(2-oxopiperidin-1-yl)phenyl]-4-(tert-butyloxycarbonyl)butyramide, ESI 1039 (2 M+H⁺);
(R)-2-[(5-chlorothiophene-2-carbonyl)amino]-N-[4-(3-oxomorpholin-4-yl)phenyl]-4-(tert-butyloxycarbonylamino)butyramide, ESI 437 (M-BOC+H⁺);
(R)-2-[(5-chlorothiophene-2-carbonyl)amino]-N-[3-methyl-4-(3-oxomorpholin-4-yl)phenyl]4-(tert-butyloxycarbonylamino)butyramide, ESI 451 (M-BOC+H⁺);
(R)-2-[(5-chlorothiophene-2-carbonyl)amino]-N-[4-(3-oxomorpholin-4-yl)phenyl]-5-(tert-butyloxycarbonylamino)valeramide, ESI 451 (M-BOC+H⁺);
(R)-2-[(5-chlorothiophene-2-carbonyl)amino]-N-[3-methyl-4-(3-oxomorpholin-4-yl)phenyl]-5-(tert-butyloxycarbonylamino)valeramide, ESI 465 (M-BOC+H⁺);
(R)-2-[(5-chlorothiophene-2-carbonyl)amino]-N-[4-(3-oxomorpholin-4-yl)phenyl]-3-(tert-butyloxycarbonylamino)propionamide, ESI 423 (M-BOC+H⁺);
(R)-2-[(5-chlorothiophene-2-carbonyl)amino]-N-[3-methyl-4-(3-oxomorpholin-4-yl)phenyl]-3-(tert-butyloxycarbonylamino)propionamide, ESI 437 (M-BOC+H⁺);
(R)-3-[(5-chlorothiophene-2-carbonyl)amino]-N-[3-methyl-4-(3-oxomorpholin-4-yl)phenyl]butyramide, ESI 436;
(R)-3-[(5-chlorothiophene-2-carbonyl)amino]-N-[3-methyl-4-(3-oxomorpholin-4-yl)phenyl]-5-methyladipamide, ESI 478;
(S)-3-[(5-chlorothiophene-2-carbonyl)amino]-N-[3-methyl-4-(3-oxomorpholin-4-yl)phenyl]-5-methyladipamide, ESI 478;
(R)-2-[(5-chlorothiophene-2-carbonyl)amino]-N-[4-(2-oxo-2H-pyridin-1-yl)phenyl]-3-methoxypropionamide, m.p. 123-127°;
(R)-2-[(5-chlorothiophene-2-carbonyl)amino]-N-[3-methyl-4-(3-oxomorpholin-4-yl)phenyl]-3-methoxypropionamide, m.p. 74-81°;
(2R,3R)-2-[(5-chlorothiophene-2-carbonyl)amino]-N-[4-(3-oxomorpholin-4-yl)phenyl]-3-methoxybutyramide, ESI 452;
(2R,3)-2-[(5-chlorothiophene-2-carbonyl)amino]-N-[3-methyl-4-(3-oxomorpholin-4-yl)phenyl]-3-methoxybutyramide, ESI 466;
(S)-2-[(5-chlorothiophene-2-carbonyl)amino]-N-[3-methyl-4-(3-oxomorpholin-4-yl)phenyl]-3-methoxypropionamide, ESI 452;
(R)-2-[(5-chlorothiophene-2-carbonyl)amino]-N-[3-trifluoromethyl-4-(3-oxomorpholin-4-yl)phenyl]-3-methoxypropionamide, ESI 506;
(R)-2-[(5-chlorothiophene-2-carbonyl)amino]-N-[3-chloro-4-(2-azabicyclo[2.2.2]octan-2-yl)phenyl]-3-methoxypropionamide, ESI 496;
(R)-2-[(5-chlorothiophene-2-carbonyl)amino]-N-[3-trifluoromethoxy-4-(2-azabicyclo[2.2.2]octan-2-yl)phenyl]-3-methoxypropionamide, ESI 530;
(R)-2-[(5-chlorothiophene-2-carbonyl)amino]-N-[3-chloro-4-(3-oxomorpholin-4-yl)phenyl]-3-methoxypropionamide, ESI 472;
(R)-2-[(5-chlorothiophene-2-carbonyl)amino]-N-[3-fluoro-4-(3-oxomorpholin-4-yl)phenyl]-3-methoxypropionamide, ESI 456;
(R)-2-[(5-chlorothiophene-2-carbonyl)amino]-N-[3-chloro-4-(2-oxo-2H-pyridin-1-yl)phenyl]-3-methoxypropionamide, ESI 466;
(R)-2-[(5-chlorothiophene-2-carbonyl)amino]-N-[3-methyl-4-(3-oxomorpholin-4-yl)phenyl]-3-allylpropionamide, ESI 478;
(R)-2-[(5-chlorothiophene-2-carbonyl)amino]-N-[3-methyl-4-(3-oxomorpholin-4-yl)phenyl]-3-propoxypropionamide, ESI 480;
(R)-2-[(5-chlorothiophene-2-carbonyl)amino]-N-[3-methyl-4-(3-oxomorpholin-4-yl)phenyl]-3-ethoxypropionamide, ESI 466;
(R)-2-[(5-chlorothiophene-2-carbonyl)amino]-N-[3-methyl-4-(3-oxomorpholin-4-yl)phenyl]-3-(2-methoxyethoxy)propionamide, ESI 496;
(2R,3)-2-[(5-chlorothiophene-2-carbonyl)amino]-N-[3-methyl-4-(3-oxomorpholin-4-yl)phenyl]-3-ethoxybutyramide, ESI 480;
(2R,3)-2-[(5-chlorothiophene-2-carbonyl)amino]-N-[3-methyl-4-(3-oxomorpholin-4-yl)phenyl]-3-(2-methoxyethoxy)butyramide, ESI 510.

EXAMPLE 2

The preparation of (R)-2-[(4-chlorophenylcarbonyl)amino]-N-[4-(3-oxomorpholin-4-yl)phenyl]4-methylvaleramide is carried out analogously to the following scheme:

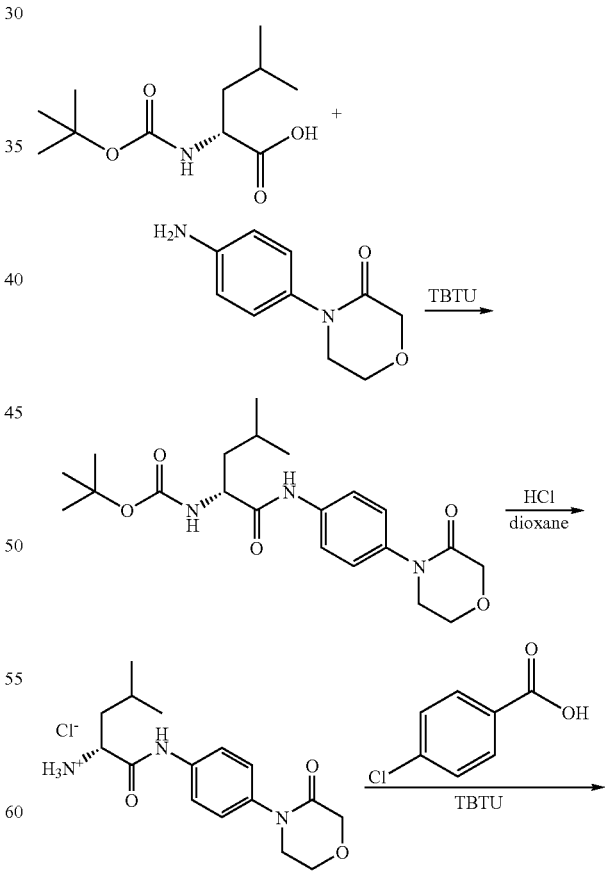

-continued

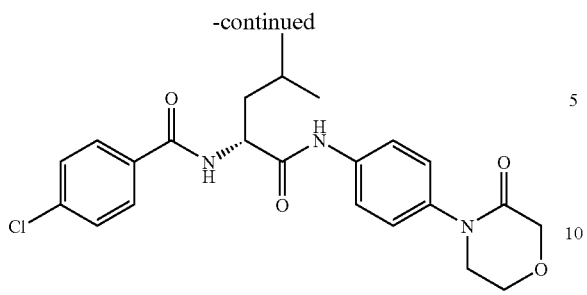

3.52 g (11.0 mmol) of 2-(1H-benzotriazol-1-yl)-1,1,3,3-tetramethyluronium tetrafluoroborate (TBTU) are added to a solution of 2.28 g (9.15 mmol) of Boc-D-leucine hydrate and 1.76 g (27.5 mmol) of 4-(4-aminophenyl)morpholin-3-one in 10 ml of DMF, and the mixture is stirred at room temperature for 18 hours. Saturated aqueous sodium hydrogencarbonate solution is added to the reaction mixture, and the precipitate formed is filtered off, washed with water and dried: tert-butyl (R)-{3-methyl-1-[4-(3-oxomorpholin-4-yl)phenylcarbamoyl]butyl}carbamate as colourless solid; ESI 406.

20 ml of 4 N HCl in dioxane are added to 1.10 g (2.71 mmol) of tert-butyl (R)-{3-methyl-1-[4-(3-oxomorpholin-4-yl)phenylcarbamoyl]butyl}carbamate, and the mixture is stirred at room temperature for 18 hours. The reaction mixture is evaporated: N-[4-(3-oxomorpholin-4-yl)phenyl]-(R)-2-amino-4-methylpentanamide hydrochloride as slightly reddish solid; ESI 306.

54.6 mg (0.540 mmol) of 4-methylmorpholine and 173 mg (0.540 mmol) of 2-(1H-benzotriazol-1-yl)-1,1,3,3-tetramethyluronium tetrafluoroborate (TBTU) are added to a solution of 140 mg (0.410 mmol) of N-[4-(3-oxomorpholin-4-yl)phenyl]-(R)-2-amino-4-methylpentanamide hydrochloride and 64.2 mg (0.410 mmol) of 4-chlorobenzoic acid in 2 ml of dimethylformamide (DMF), and the mixture is stirred at room temperature for 18 hours. Saturated aqueous sodium hydrogencarbonate solution is added to the reaction mixture, and the precipitate formed is filtered off, washed with water and dried: (R)-2-[(4-chlorophenylcarbonyl)amino]-N-[4-(3-oxomorpholin-4-yl)phenyl]4-methylvaleramide as colourless solid; ESI 444.

(R)-2-[(4-chlorophenylcarbonyl)amino]-N-[3-methyl-4-(3-oxomorpholin-4-yl)phenyl]-4-methylvaleramide is obtained analogously.

EXAMPLE 2-1

The preparation of (R)-2-[(5-chlorothiophene-2-carbonyl)amino]-N-[3-methyl-4-(3-oxomorpholin-4-yl)phenyl]-3-methylsulfonylpropionamide, ESI 500; is carried out analogously to the following scheme, where the sulfanil compound to be oxidised is obtained analogously to Example 1:

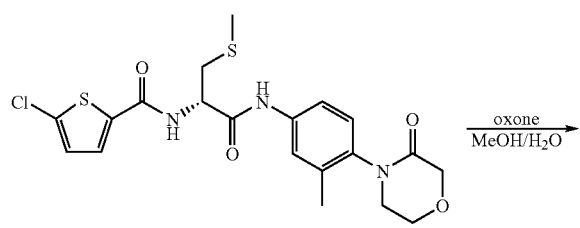

-continued

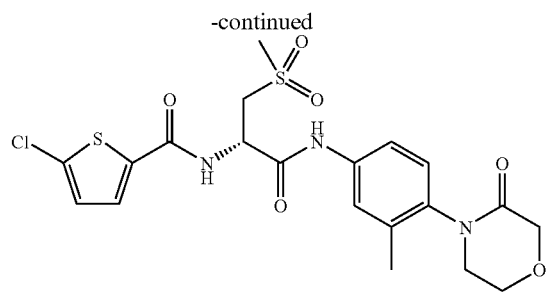

The following compounds are obtained analogously
(R)-2-[(5-chlorothiophene-2-carbonyl)amino]-N-[4-(2-oxo-2H-pyridin-1-yl)phenyl]-3-methylsulfonylpropionamide, ESI 480;
(R)-2-[(5-chlorothiophene-2-carbonyl)amino]-N-[4-(3-oxomorpholin-4-yl)phenyl]-3-methylsulfonylpropionamide, ESI 486;
(R)-2-[(5-chlorothiophene-2-carbonyl)amino]-N-[4-(3-oxomorpholin-4-yl)phenyl]-3-methylsulfonylbutyramide, ESI 500;
(R)-2-[(5-chlorothiophene-2-carbonyl)amino]-N-[3-methyl-4-(3-oxomorpholin-4-yl)phenyl]-3-methylsulfonylbutyramide, ESI 514;
(R)-2-[(5-chlorothiophene-2-carbonyl)amino]-N-[4-(2-oxo-2H-pyridin-1-yl)phenyl]-3-methylsulfonylbutyramide, ESI 494;

EXAMPLE 2-2

The preparation of (R)-2-[(5-chlorothiophen-2-ylmethyl)amino]-N-[4-(3-oxomorpholin-4-yl)phenyl]valeramide is carried out analogously to the following scheme:

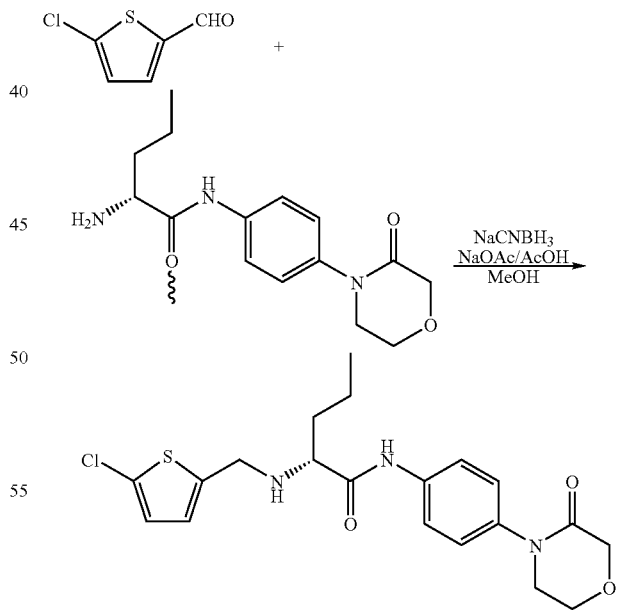

230 mg (0.789 mmol) of (R)-2-amino-N-[4-(3-oxomorpholin-4-yl)phenyl]-pentanamide, 70 mg (0.853 mmol) of sodium acetate and 48 μl (0.839 mmol) of acetic acid are added at room temperature under nitrogen to a solution of 120 mg (0.819 mmol) of 5-chloro-2-thiophenecarboxaldehyde in 5 ml of methanol, and the mixture is stirred at room temperature for 30 min. 52.0 mg (0.827 mmol) of sodium cyanoborohydride is added slowly to this solution, and the resultant suspension is stirred at room temperature for 24 hours. The reaction mixture is evaporated and partitioned between ethyl acetate and dilute sodium hydrogencarbonate solution. The organic phase is dried over sodium sulfate and evaporated: (R)-2-([(5-chlorothiophen-2-ylmethyl)amino]-N-[4-(3-oxomorpholin-4-yl)phenyl]valeramide as colourless oil; ESI 422.

EXAMPLE 2-3

The preparation of (R)-2-[(5-chlorothiophene-2-carbonyl)amino]-N-[4-(3-oxomorpholin-4-yl)phenyl]-3-carboxypropionamide, ESI 452, is carried out analogously to the following scheme:

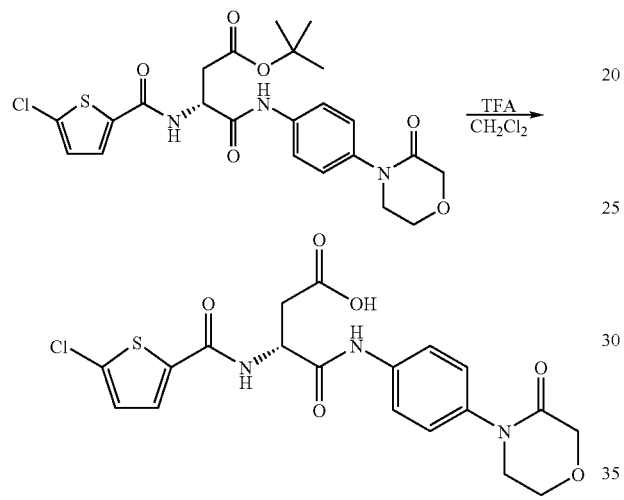

The following compounds are obtained analogously
- (R)-2-[(5-chlorothiophene-2-carbonyl)amino]-N-[3-methyl-4-(3-oxomorpholin-4-yl)phenyl]-3-carboxypropionamide, ESI 466;
- (R)-2-[(5-chlorothiophene-2-carbonyl)amino]-N-[4-(3-oxomorpholin-4-yl)phenyl]4-carboxybutyramide, ESI 466;
- (R)-2-[(5-chlorothiophene-2-carbonyl)amino]-N-[3-methyl-4-(3-oxomorpholin-4-yl)phenyl]-4-carboxybutyramide, ESI 480.

EXAMPLE 2-4

The preparation of (R)-2-[(5-chlorothiophene-2-carbonyl)amino]-N-[4-(3-oxomorpholin-4-yl)phenyl]4-aminobutyramide, trifluoroacetate, ESI 437, is carried out analogously to the following scheme:

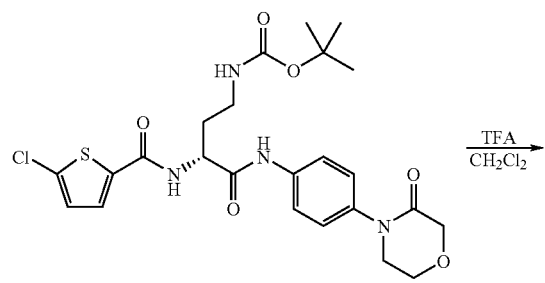

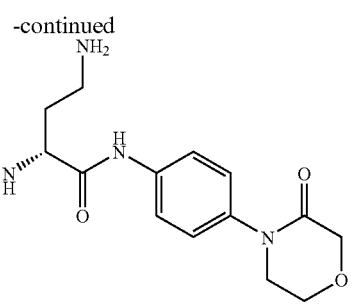

trifluoroacetate

The following compounds are obtained analogously
- (R)-2-[(5-chlorothiophene-2-carbonyl)amino]-N-[3-methyl-4-(3-oxomorpholin-4-yl)phenyl]4-aminobutyramide, trifluoroacetate, ESI 451;
- (R)-2-[(5-chlorothiophene-2-carbonyl)amino]-N-[4-(3-oxomorpholin-4-yl)phenyl]-5-aminovaleramide, trifluoroacetate, ESI 451;
- (R)-2-[(5-chlorothiophene-2-carbonyl)amino]-N-[3-methyl-4-(3-oxomorpholin-4-yl)phenyl]-5-aminovaleramide, trifluoroacetate, ESI 465;
- (R)-2-[(5-chlorothiophene-2-carbonyl)amino]-N-[4-(3-oxomorpholin-4-yl)phenyl]-3-aminopropionamide, trifluoroacetate, ESI 423;
- (R)-2-[(5-chlorothiophene-2-carbonyl)amino]-N-[3-methyl-4-(3-oxomorpholin-4-yl)phenyl]-3-aminopropionamide, trifluoroacetate, ESI 437.

3. Examples of the Preparation of Intermediate Compounds 3.1 All Compounds of the following formula VI (where R=H or methyl; n=3, 4 or 5) can be synthesised in accordance with the following scheme

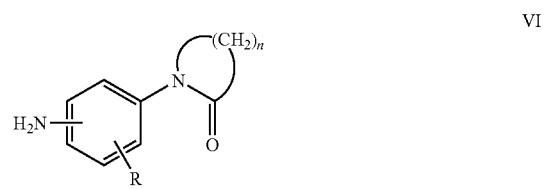

For example synthesis of 1-(4-amino-2-methylphenyl)piperidin-2-one:

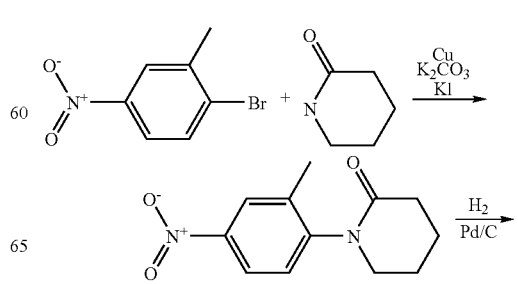

3.2 Synthesis of the phenylpiperidone unit without methyl group:
The preparation of 1-(4-amino-2-methylphenyl)piperidin-2-one is carried out, for example, as indicated below:
3.3 1-(4-Aminophenyl)-1H-pyrazin-2-one
3.4 1-(4-Amino-2,5-dimethylphenyl)piperidin-2-one
3.5 1-(4-Amino-3-methylphenyl)piperidin-2-one
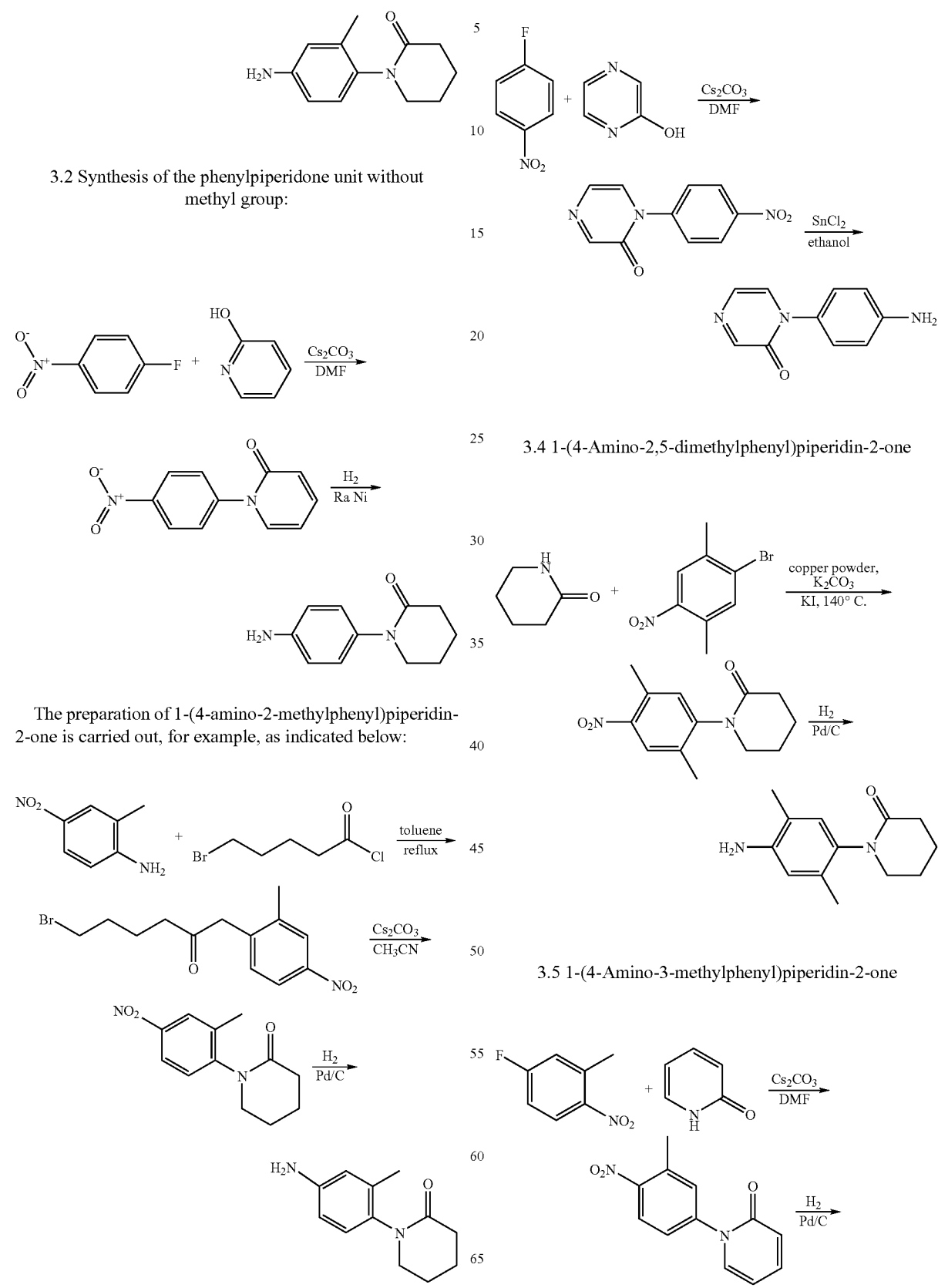

3.6 1-(5-Aminopyridin-2-yl)piperidin-2-one
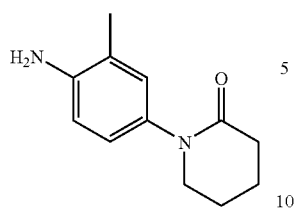
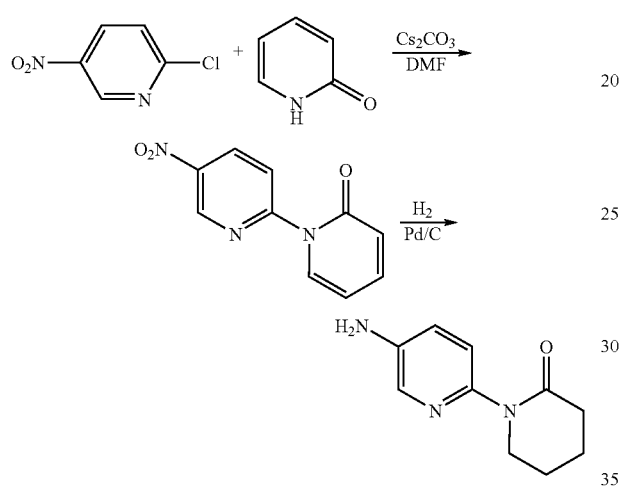
3.7 1-(4-Aminomethylphenyl)piperidin-2-one
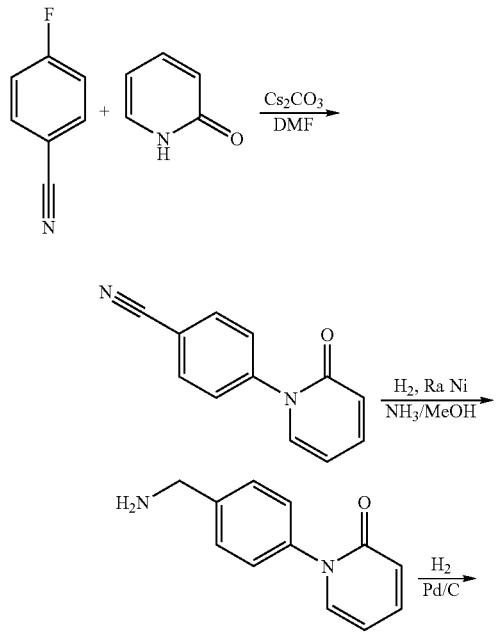
3.8 2-(4-Aminophenyl)-2-azabicyclo[2.2.2]octan-3-one
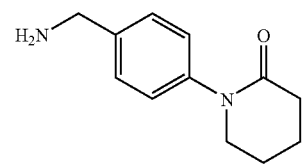
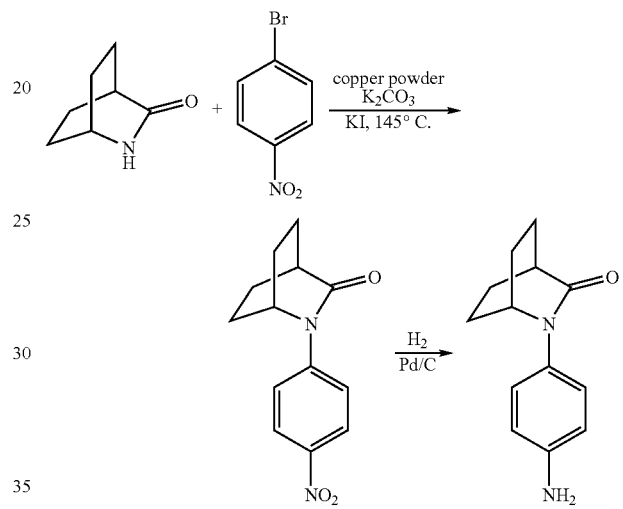
3.9 1-(3-Amino-6-ethylphenyl)pyrrolidin-2-one
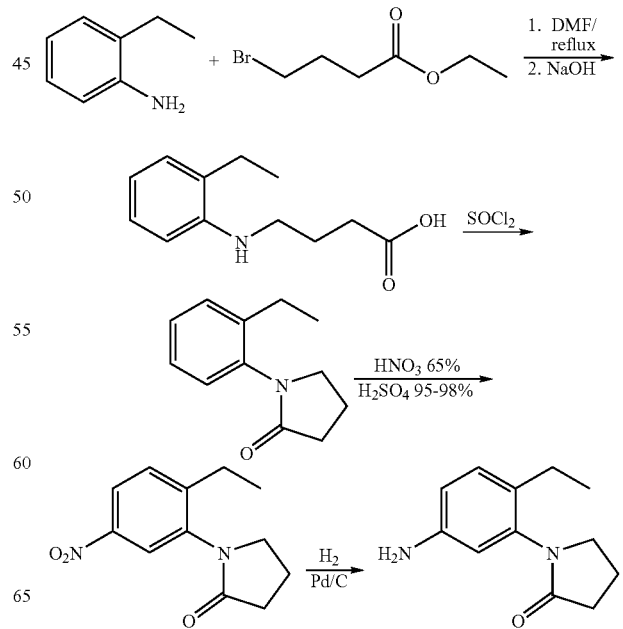

3.10 2-(4-Amino-2-trifluoromethylphenyl)-2-azabicyclo[2.2.2]octan-3-one
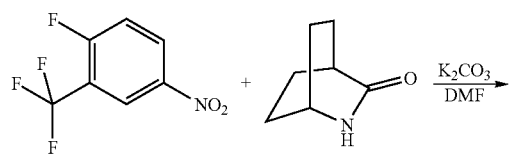
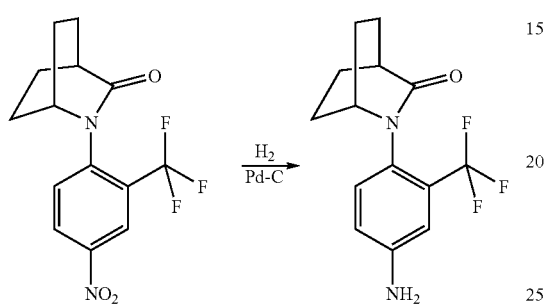
3.11 1-(4-Amino-3-chlorophenyl)pyrrolidin-2-one
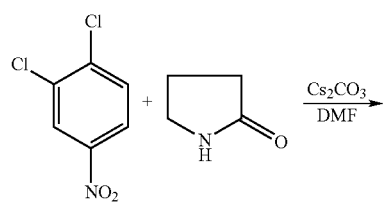
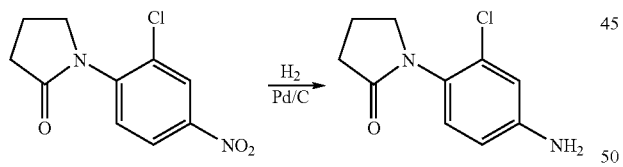
3.12 1-(4-Amino-2-trifluoromethylphenyl)piperidin-2-one
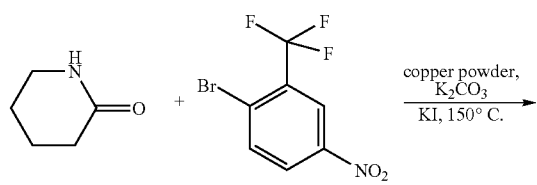
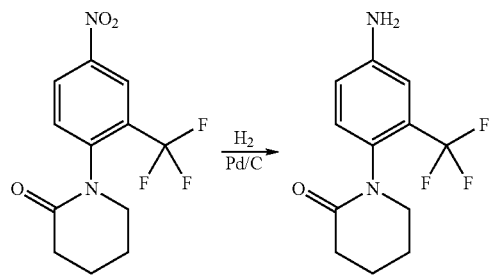
3.13 3-(4-Amino-2-methylphenyl)-1,3-oxazinan-2-one
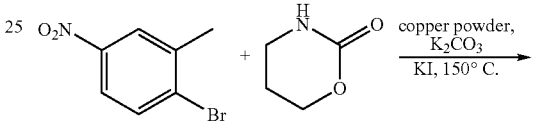
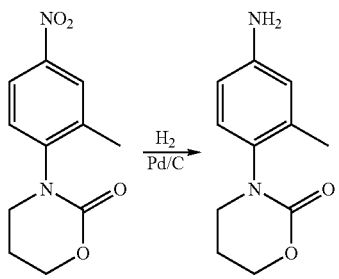
3.14 4-(4-Aminophenyl)morpholin-3-one
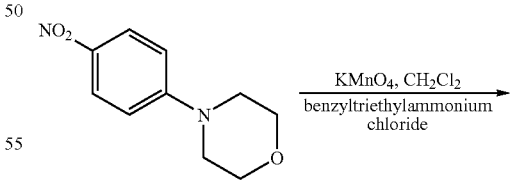
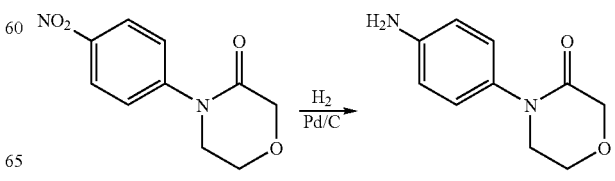

3.15 1-(4-Aminophenyl)pyridin-2-one
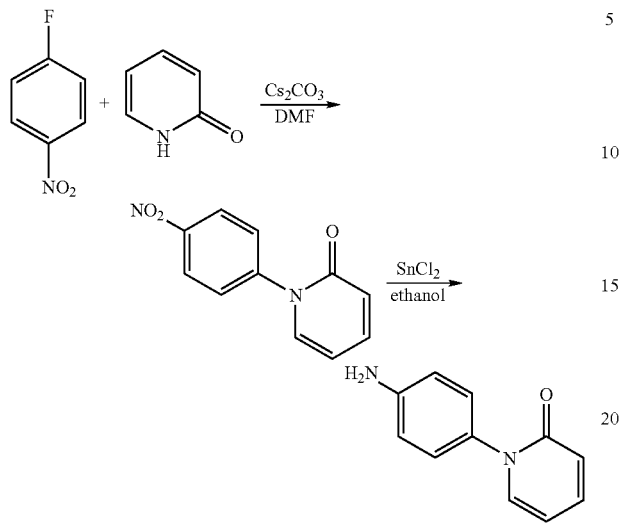
3.16 1-(4-Amino-2-methylphenyl)piperidin-2-one
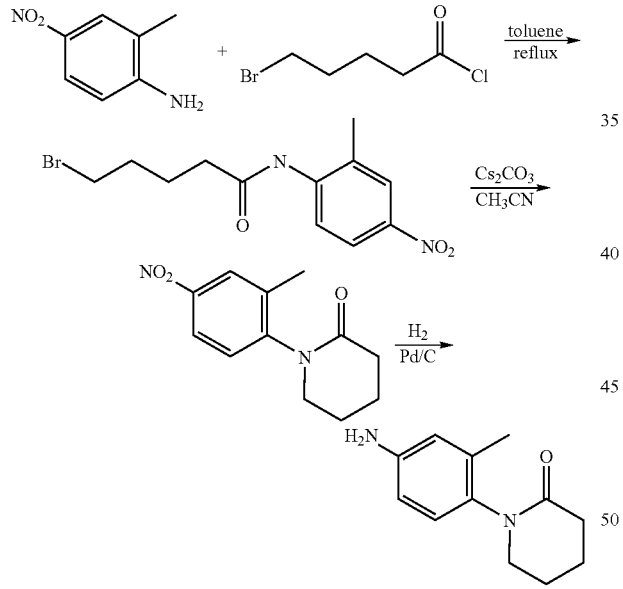
3.17 1-(4-Aminophenyl)-1H-pyridin-4-one
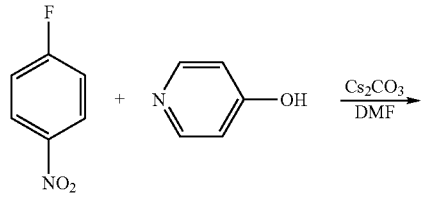
-continued
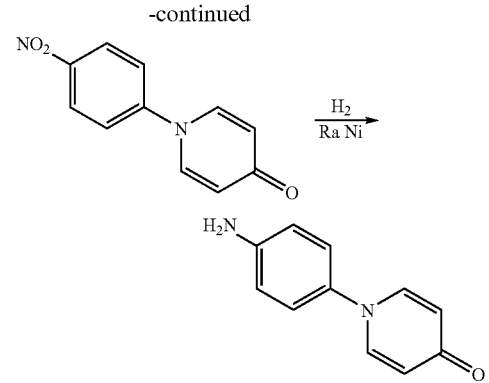
3.18 1-(4-Aminophenyl)-4-tert-butyloxycarbonylpiperazin-2-one
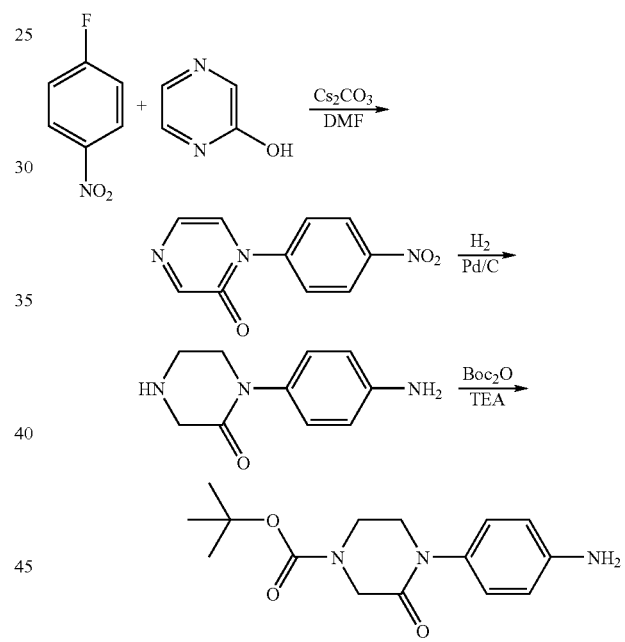
3.19 1-(3-Aminophenyl)piperidin-2-one
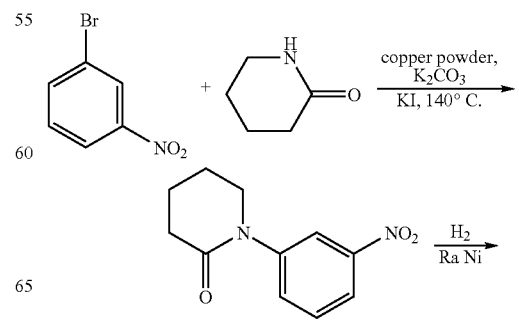

3.20 1-(4-Aminophenyl)-2-caprolactam
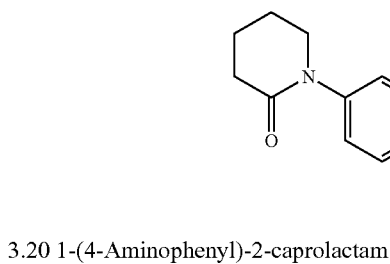
3.21 1-(4-Amino-3-fluorophenyl)piperidin-2-one
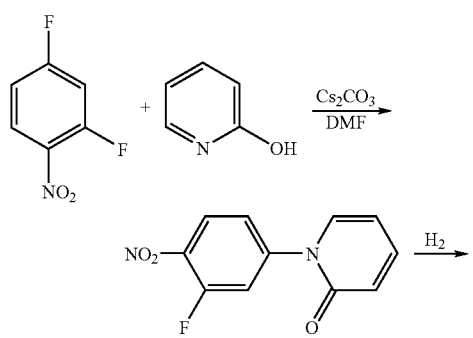
3.22 1-(4-Amino-2-fluorophenyl)piperidin-2-one
3.23 1-(4-Amino-2-fluoro)-2-caprolactam
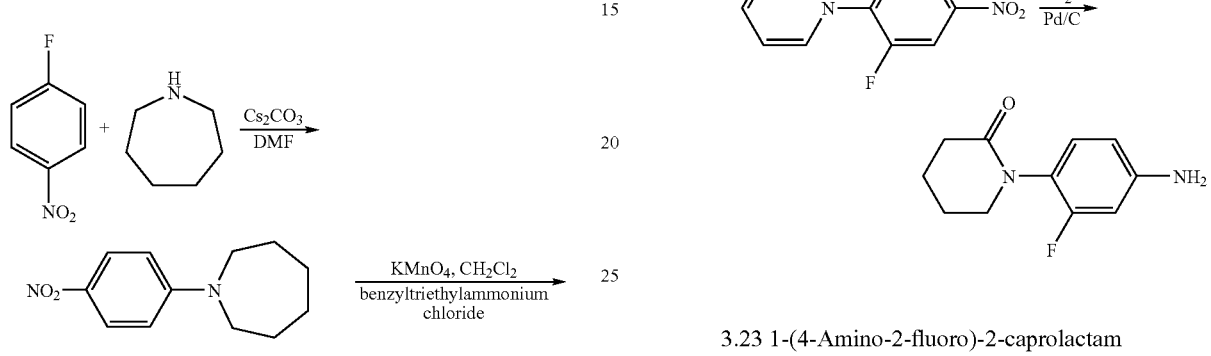
3.24 4-(2-Iminopiperidin-1-yl)aniline, hydrochloride

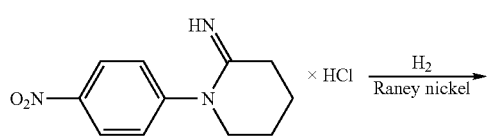

EXAMPLE 4

The preparation of (R)-2-[(5-chlorothiophene-2-carbonyl)amino]-N-[4-(2-iminopiperidin-1-yl)phenyl]-4-methylvaleramide and (S)-2-[(5-chlorothiophene-2-carbonyl)amino]-N-[4-(2-iminopiperidin-1-yl)phenyl]-4-methylvaleramide is carried out analogously to the following scheme:

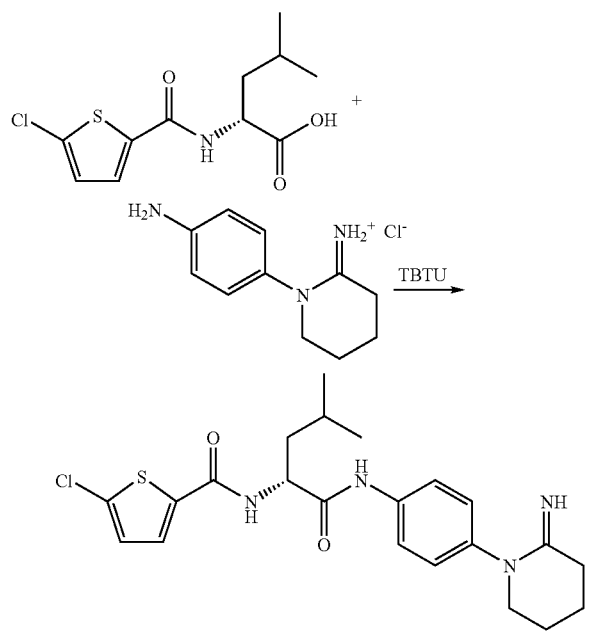

(R)-2-[(5-chlorothiophene-2-carbonyl)amino]-N-[4-(2-iminopiperidin-1-yl)phenyl]-4-methylvaleramide ("4A"), ESI 447;

(S)-2-[(5-chlorothiophene-2-carbonyl)amino]-N-[4-(2-iminopiperidin-1-yl)phenyl]-4-methylvaleramide ("4B"), ESI 447.

EXAMPLE 5

The preparation of (R)-2-[(5-chlorothiophene-2-carbonyl)amino]-N-[3-methyl-4-(3-oxomorpholin-4-yl)phenyl]-3-hydroxypropionamide is carried out as indicated below:

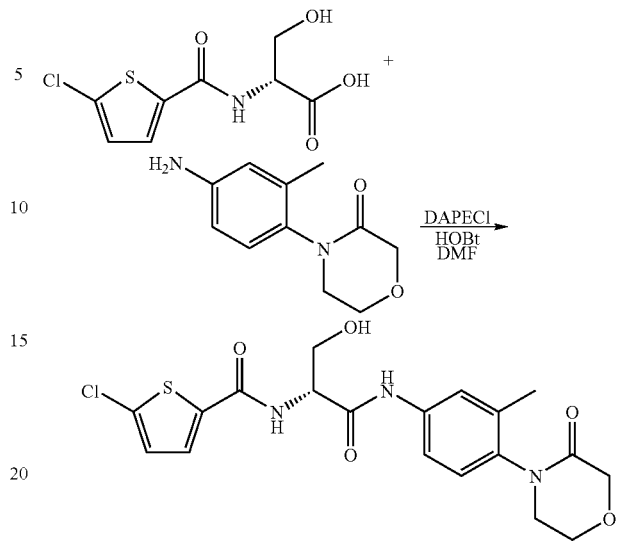

211 mg (1.10 mmol) of N-(3-dimethylaminopropyl)-N'-ethylcarbodiimide hydrochloride (DAPECI) are added at room temperature to a solution of 250 mg (1.00 mmol) of (R)-2-[(5-chlorothiophene-2-carbonyl)amino]-3-hydroxypropionic acid, 206 mg (1.00 mmol) of 4-(4-amino-2-methylphenyl)morpholin-3-one and 169 mg (1.10 mmol) of hydroxybenzotriazole hydrate in 6 ml of DMF, and the mixture is stirred at room temperature for 48 hours. 100 ml of dilute sodium hydrogencarbonate solution are added to the reaction mixture, and the resultant precipitate is filtered off and dried: (R)-2-[(5-chlorothiophene-2-carbonyl)amino]-N-[3-methyl-4-(3-oxomorpholin-4-yl)phenyl]-3-hydroxypropionamide as colourless solid; ESI 438.

The following compounds are obtained analogously (R)-2-[(5-chlorothiophene-2-carbonyl)amino]-N-[3-4-(3-oxomorpholin-4-yl)phenyl]-3-hydroxypropionamide, m.p. 227-233°;

(2R,3)-2-[(5-chlorothiophene-2-carbonyl)amino]-N-[4-(3-oxomorpholin-4-yl)phenyl]-3-hydroxybutyramide, m.p. 198-200°.

EXAMPLE 6

The preparation of (2R,3)-2-[(5-chlorothiophene-2-carbonyl)amino]-N-[4-(3-oxomorpholin-4-yl)phenyl]-3-aminocarbonyloxybutyramide, ESI 481 is carried out as indicated below:

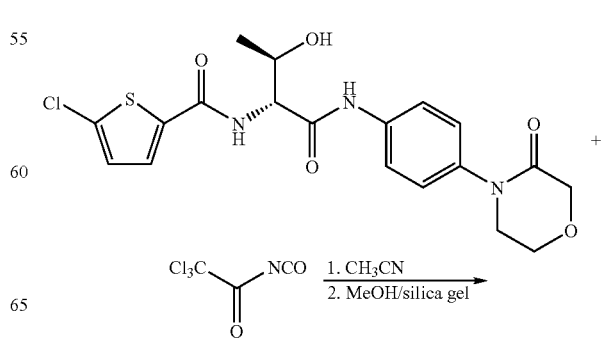

-continued

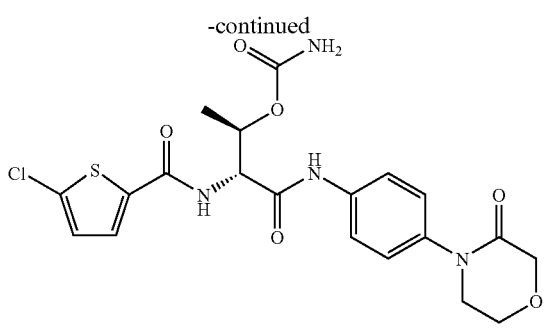

The following compounds are obtained analogously
(2R)-2-[(5-chlorothiophene-2-carbonyl)amino]-N-[3-methyl-4-(3-oxomorpholin-4-yl)phenyl]-3-aminocarbonyloxypropionamide, m.p. 211-215°;
(2R,3)-2-[(5-chlorothiophene-2-carbonyl)amino]-N-[3-methyl-4-(3-oxomorpholin-4-yl)phenyl]-3-aminocarbonyloxybutyramide, m.p. 167-170°.

| Pharmacological data (affinity to receptors) | | |
|---|---|---|
| Compound No. | $FXa\text{-}IC_{50}$ [M] | $TF/FVIIa\text{-}IC_{50}$ [M] |
| "1A" | $7.3 \times 10^{-9}$ | $6.9 \times 10^{-9}$ |
| "2A" | $3.9 \times 10^{-8}$ | |
| "4A" | $2.5 \times 10^{-8}$ | |
| "4B" | $2.6 \times 10^{-7}$ | |

The following examples relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

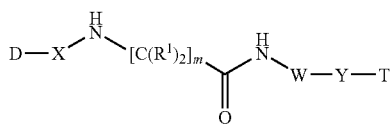

in which
D denotes thienyl which is unsubstituted or mono- or polysubstituted by Hal, A, $OR^2$, $N(R^2)_2$, $NO_2$, CN, $COOR^2$ or $CON(R^2)_2$,
X denotes —C═O,
W denotes —[C(R$^3$)$_2$]$_n$—,
R$^1$ denotes H or A, which may be substituted by $OR^3$, $S(O)_n R^3$, $N(R^3)_2$, CN, $COOR^3$, $CON(R^3)_2$, $OCON(R^3)_2$, $N(R^3)COOR^3$, $N(R^3)CON(R^3)_2$, $N(R^3)SO_2R^3$, $SO_2N(R^3)_2$ or —C≡C—,
R$^2$ denotes H, A, —[C(R$^3$)$_2$]$_n$—Ar', —[C(R$^3$)$_2$]$_n$-Het', —[C(R$^3$)$_2$]$_n$-cycloalkyl, —[C(R$^3$)$_2$]$_n$—N(R$^3$)$_2$ or —[C(R$^3$)$_2$]$_n$—OR$^3$,
R$^3$ denotes H or A, Y denotes Ar-diyl, T denotes a mono- or bicyclic saturated, unsaturated or aromatic carbo- or heterocycle having 0 to 4 N, O and/or S atoms which is mono- or disubstituted by =O, =S, =NR$^2$, =N—CN, =N—NO$_2$, =NOR$^2$, =NCOR$^2$, =NCOOR$^2$, and/or =NOCOR$^2$ and may furthermore be mono-, di- or trisubstituted by R$^2$, Hal, A, —[C(R$^3$)$_2$]$_n$—Ar, —[C(R$^3$)$_2$]$_n$-Het, —[C(R$^3$)$_2$]$_n$-cycloalkyl, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$NR$^2$ and/or S(O)$_n$A, A denotes unbranched or branched alkyl having 1-10 C atoms, in which one or two CH$_2$ groups may be replaced by O or S atoms and/or by —CH=CH— groups and/or 1-7 H atoms may be replaced by F, Ar denotes phenyl, naphthyl or biphenyl, each of which is unsubstituted or mono-, di- or trisubstituted by Hal, A, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$N(R$^2$)$_2$, S(O)$_n$A, —[C(R$^3$)$_2$]$_n$—COOR$^2$ or —O—[C(R$^3$)$_2$]$_o$—COOR$^2$, Ar' denotes phenyl which is unsubstituted or mono-, di- or trisubstituted by Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$, S(O)$_n$A, —[C(R$^3$)$_2$]$_n$—COOR$^3$ or —O—[C(R$^3$)$_2$]$_o$—COOR$^3$, Het denotes a mono- or bicyclic saturated, unsaturated or aromatic heterocycle having 1 to 4 N, O and/or S atoms, which may be unsubstituted or mono-, di- or trisubstituted by carbonyl oxygen, =S, =N(R$^2$)$_2$, Hal, A, —[C(R$^3$)$_2$]$_n$—Ar, —[C(R$^3$)$_2$]$_n$-Het', —[C(R$^3$)$_2$]$_n$-cycloalkyl, —[C(R$^3$)$_2$]$_n$—OR$^2$, —[C(R$^3$)$_2$]$_n$—N(R$^3$)$_2$, NO$_2$, CN, —[C(R$^3$)$_2$]$_n$—COOR$^{2'}$, —[C(R$^3$)$_2$]$_n$—CON(R$^2$)$_2$, —[C(R$^3$)$_2$]$_n$—NR$^2$COA, NR$^2$CON(R$^2$)$_2$, —[C(R$^3$)$_2$]$_n$—NR$^2$SO$_2$A, COR$^2$, SO$_2$NR$^2$ and/or S(O)$_n$A, Het' denotes a mono- or bicyclic saturated, unsaturated or aromatic heterocycle having 1 to 4 N, O and/or S atoms, which may be unsubstituted or mono- or disubstituted by carbonyl oxygen, =S, =N(R$^3$)$_2$, Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^3$ and/or S(O)$_n$A, Hal denotes F, Cl, Br or I, m denotes 1 or 2, n denotes 0, 1 or 2, and o denotes 1, 2 or 3, or a pharmaceutically acceptable salt, or stereoisomer thereof, or a mixture thereof.

2. A compound according to claim 1, in which

D denotes thienyl which is unsubstituted or mono- or disubstituted by Hal, or a pharmaceutically acceptable salt or stereoisomer thereof, or a mixture thereof.

3. A compound according to claim 1, in which

D denotes thienyl which is mono- or disubstituted by Hal, or a pharmaceutically acceptable salt or stereoisomer thereof, or a mixture thereof.

4. A compound according to claim 1, in which

R$^2$ denotes H or alkyl having 1, 2, 3, 4, 5 or 6 C atoms, or a pharmaceutically acceptable salt or stereoisomer thereof, or a mixture thereof.

5. A compound according to claim 1, in which

R$^1$ denotes H or A, which may be substituted by OR$^3$, CON(R$^3$)$_2$, N(R$^3$)$_2$, S(O)$_n$R$^3$, COOR$^3$, OCON(R$^3$)$_2$, N(R$^3$)COOR$^3$ or —C≡C—, or a pharmaceutically acceptable salt or stereoisomer thereof, or a mixture thereof.

6. A compound according to claim 1, in which

W is absent, or a pharmaceutically acceptable salt or stereoisomer thereof, or a mixture thereof.

7. A compound according to claim 1, in which

T denotes a mono- or bicyclic saturated, unsaturated or aromatic heterocycle having 1 to 2 N and/or O atoms which is mono- or disubstituted by =O, =S, =NR$^2$, =N—CN, =N—NO$_2$, =NOR$^2$, =NCOR$^2$, =NCOOR$^2$ or =NOCOR$^2$ and may furthermore be mono- or disubstituted by Hal or A, or a pharmaceutically acceptable salt or stereoisomer thereof, or a mixture thereof.

8. A compound according to claim 1, in which

T denotes a mono- or bicyclic saturated or unsaturated heterocycle having 1 to 2 N and/or O atoms which is mono- or disubstituted by =O, =S or =NH, or a pharmaceutically acceptable salt or stereoisomer thereof, or a mixture thereof.

9. A compound according to claim 1, in which

T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo[2.2.2]-octan-2-yl, each of which is mono- or disubstituted by =O or =NH, or a pharmaceutically acceptable salt or stereoisomer thereof, or a mixture thereof.

10. A compound according to claim 1, in which

Ar denotes phenyl which is unsubstituted or mono- or disubstituted by Hal, A, OA, SO$_2$A, COOR$^2$, SO$_2$NH$_2$ or CN, or a pharmaceutically acceptable salt or stercoisomer thereof, or a mixture thereof.

11. A compound according to claim 1, in which

Ar denotes phenyl which is unsubstituted or mono- or disubstituted by A and/or Hal, or a pharmaceutically acceptable salt or stereoisomer thereof, or a mixture thereof.

12. A compound according to claim 1, in which

D denotes thienyl which is unsubstituted or mono- or disubstituted by Hal,

R$^1$ denotes H or A, which may be substituted by OR$^3$, CON(R$^3$)$_2$, N(R$^3$)$_2$, S(O)$_n$R$^3$, COOR$^3$, OCON(R$^3$)$_2$, N(R$^3$)COOR$^3$ or —C≡C—, R$^2$ denotes H or alkyl having 1, 2, 3, 4, 5 or 6 C atoms, X denotes —C=O, W is absent, Y denotes Ar-diyl, Ar denotes phenyl which is unsubstituted or mono- or disubstituted by A and/or Hal, and T denotes a mono- or bicyclic saturated or unsaturated heterocycle having 1 to 2 N and/or O atoms which is mono- or disubstituted by =O, =S or =NH, or a pharmaceutically acceptable salt or stereoisomers thereof, or a mixture thereof.

13. A compound according to claim 1, in which

D denotes thienyl which is mono- or disubstituted by Hal,

R$^1$ denotes H or A, which may be substituted by OR$^3$, CON(R$^3$)$_2$, N(R$^3$)$_2$, S(O)$_n$R$^3$, COOR$^3$, OCON(R$^3$)$_2$, N(R$^3$)COOR$^3$ or —C≡C—, R$^2$ denotes H or alkyl having 1, 2, 3, 4, 5 or 6 C atoms, X denotes —C=O, W is absent, Y denotes Ar-diyl, Ar denotes phenyl which is unsubstituted or mono- or disubstituted by A and/or Hal, and T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo-[2.2.2]octan-2-yl, each of which is mono- or disubstituted by =O or =NH, or a pharmaceutically acceptable salt or stereoisomer thereof, or a mixture thereof.

14. A compound according to claim 1, in which

D denotes thienyl which is mono- or disubstituted by Hal,
$R^1$ denotes H or A, which may be substituted by $OR^3$, $CON(R^3)_2$, $N(R^3)_2$, $S(O)_nR^3$, $COOR^3$, $OCON(R^3)_2$, $N(R^3)COOR^3$ or —C≡C—,
$R^2$ denotes H or alkyl having 1, 2, 3, 4, 5 or 6 C atoms,
$R^3$ denotes H or alkyl having 1, 2, 3, 4, 5 or 6 C atoms,
X denotes —C=O,
W is absent or denotes $CH_2$,
Y denotes Ar-diyl
A denotes alkyl having 1, 2, 3, 4, 5 or 6 C atoms, in which one or two $CH_2$ groups may be replaced by O or S atoms and/or by —CH=CH— groups and/or also 1-7 H atoms may be replaced by F,
Ar denotes phenyl which is unsubstituted or mono- or disubstituted by A and/or Hal, and
T denotes piperidin-1-yl, pyrrolidin-1-yl, pyridin-1-yl, morpholin-4-yl, piperazin-1-yl, 1,3-oxazolidin-3-yl, pyridazin-2-yl, pyrazin-1-yl, azepan-1-yl or 2-azabicyclo-[2.2.2]octan-2-yl, each of which is mono- or disubstituted by =O or =NH, or a pharmaceutically acceptable salt or stereoisomer thereof, or a mixture thereof.

15. A compound, which is (S)-2-([(5-chlorothiophene-2-carbonyl)amino]-N-[4-(3-oxomorpholin-4-yl)phenyl]-4-methylvaleramide,
(S)-2-[(5-chlorothiophene-2-carbonyl)amino]-N-[3-methyl-4-(3-oxomorpholin-4-yl)phenyl]-4-methylvaleramide,
(S)-2-[(5-chlorothiophene-2-carbonyl)amino]-N-[4-(2-oxo-2H-pyrazin-1-yl)phenyl]-4-methylvaleramide,
(R)-2-[(5-chlorothiophene-2-carbonyl)amino]-N-[4-(3-oxomorpholin-4-yl)phenyl]-4-methylvaleramide,
(R)-2-[(5-chlorothiophene-2-carbonyl)amino]-N-[3-methyl-4-(3-oxomorpholin-4-yl)phenyl]-4-methylvaleramide,
(R)-2-[(5-chlorothiophene-2-carbonyl)amino]-N-[4-(2-oxo-2H-pyrazin-1-yl)phenyl]-4-methylvaleramide,
(R)-2-[(5-chlorothiophene-2-carbonyl)amino]-N-[4-(2-oxo-2H-pyridin-1-yl)phenyl]-4-methylvaleramide,
(R)-2-[(5-chlorothiophene-2-carbonyl)amino]-N-[4-(2-iminopiperidin-1-yl)phenyl]-4-methylvaleramide,
(S)-2-[(5-chlorothiophene-2-carbonyl)amino]-N-[4-(2-iminopiperidin-1-yl)phenyl]-4-methylvaleramide,
2-[(5-chlorothiophene-2-carbonyl)amino]-N-[3-methyl-4-(2-oxopiperidin-1-yl)phenyl]acetamide,
3-[(5-chlorothiophene-2-carbonyl)amino]-N-[3-methyl-4-(2-oxopiperidin-1-yl)phenyl]propionamide,
(R)-2-[(5-chlorothiophene-2-carbonyl)amino]-N-[3-methyl-4-(3-oxomorpholin-4-yl)phenyl]propionamide,
(R)-2-[(5-chlorothiophene-2-carbonyl)amino]-N-[3-methyl-4-(3-oxomorpholin-4-yl)phenyl]-3-methylbutyramide,
(R)-2-[(5-chlorothiophene-2-carbonyl)amino]-N-[3-methyl-4-(3-oxomorpholin-4-yl)phenyl]butyramide,
(R)-2-[(5-chlorothiophene-2-carbonyl)amino]-N-[3-methyl-4-(3-oxomorpholin-4-yl)phenyl]valeramide,
(R)-2-[(5-chlorothiophene-2-carbonyl)amino]-N-[3-methyl-4-(3-oxomorpholin-4-yl)phenyl]-3-aminocarbonylpropionamide,
2-[(5-chlorothiophene-2-carbonyl)amino]-N-[3-methyl-4-(3-oxomorpholin-4-yl)phenyl]-3-(N,N-dimethylamino)propionamide,
(R)-2-[(5-bromothiophene-2-carbonyl)amino]-N-[4-(3-oxomorpholin-4-yl)phenyl]-4-methylvaleramide,
(R)-2-[(5-chlorothiophene-2-carbonyl)amino]-N-[4-(2-oxopiperidin-1-yl)benzyl]-4-methylvaleramide,
(R)-2-[(5-chlorothiophene-2-carbonyl)amino]-N-[4-(3-oxomorpholin-4-yl)phenyl]-3-methylsulfanylpropionamide,
(S)-2-[(5-chlorothiophene-2-carbonyl)amino]-N-[4-(2-oxopiperidin-1-yl)benzyl]-4-methylvaleramide,
(R)-2-[(5-chlorothiophene-2-carbonyl)amino]-N-[4-(3-oxomorpholin-4-yl)phenyl]-3-methylbutyramide,
(R)-2-[(5-chlorothiophene-2-carbonyl)amino]-N-[4-(2-oxo-2H-pyridin-1-yl)phenyl]-3-methylbutyramide,
3-[(5-chlorothiophene-2-carbonyl)amino]-N-[4-(3-oxomorpholin-4-yl)-phenyl]propionamide,
3-[(5-chlorothiophene-2-carbonyl)amino]-N-[3-methyl-4-(3-oxomorpholin-4-yl)phenyl]propionamide,
3-[(5-chlorothiophene-2-carbonyl)amino]-N-[4-(2-oxo-2H-pyridin-1-yl)phenyl]propionamide,
2-[(5-chlorothiophene-2-carbonyl)amino]-N-[3-methyl-4-(3-oxomorpholin-4-yl) phenyl]acetamide,
2-[(5-chlorothiophene-2-carbonyl)amino]-N-[4-(3-oxomorpholin-4-yl) phenyl]acetamide,
2-[(5-chlorothiophene-2-carbonyl)amino]-N-[4-(2-oxo-2H-pyridin-1-yl)phenyl]acetamide,
3-[(5-chlorothiophene-2-carbonyl)amino]-N-[4-(2-oxo-2H-pyridin-1-yl)phenyl]-2-butylpropionamide,
(R)-2-[(5-chlorothiophene-2-carbonyl)amino]-N-[4-(3-oxomorpholin-4-yl) phenyl]propionamide,
(R)-2-[(5-chlorothiophene-2-carbonyl)amino]-N-[4-(3-oxomorpholin-4-yl) phenyl]valeramide,
(R)-2-[(5-chlorothiophene-2-carbonyl)amino]-N-[4-(2-oxo-2H-pyridin-1-yl)phenyl]-3-methylsulfanylpropionamide,
(R)-2-[(5-chlorothiophene-2-carbonyl)amino]-N-[4-(2-oxo-2H-pyrazin-1-yl) phenyl]propionamide,
(R)-2-[(5-chlorothiophene-2-carbonyl)amino]-N-[4-(3-oxomorpholin-4-yl)phenyl]-4-methylsulfanylbutyramide,
(R)-2-[(5-chlorothiophene-2-carbonyl)amino]-N-[4-(3-oxomorpholin-4-yl) phenyl]butyramide,
(R)-2-[(5-chlorothiophene-2-carbonyl)amino]-N-[4-(3-oxomorpholin-4-yl)phenyl]-3-ethynylpropionamide,
(R)-2-[(5-chlorothiophene-2-carbonyl)amino]-N-[3-methyl-4-(3-oxomorpholin-4-yl) phenyl]-3-ethynylpropionamide,
(R)-2-[(5-chlorothiophene-2-carbonyl)amino]-N-[3-fluoro-4-(3-oxomorpholin-4-yl) phenyl]propionamide,
(R)-2-[(5-chlorothiophene-2-carbonyl)amino]-N-[3-methyl-4-(3-oxomorpholin-4-yl) phenyl]-4-methylsulfanylbutyramide,
(R)-2-[(5-chlorothiophene-2-carbonyl)amino]-N-[4-(3-oxomorpholin-4-yl)phenyl]-3-(tert-butyloxycarbonyl)propionamide,
(R)-2-[(5-chlorothiophene-2-carbonyl)amino]-N-[4-(3-oxomorpholin-4-yl)phenyl]-3-vinylpropionamide,
(R)-2-[(5-chlorothiophene-2-carbonyl)amino]-N-[3-methyl-4-(3-oxomorpholin-4-yl) phenyl]-3-vinylpropionamide,
(R)-2-[(5-chlorothiophene-2-carbonyl)amino]-N-[3-methyl-4-(3-oxomorpholin-4-yl) phenyl]-3-(tert-butyloxycarbonyl)propionamide,
(R)-2-[(5-chlorothiophene-2-carbonyl)amino]-N-[4-(3-oxomorpholin-4-yl)phenyl]-4-methoxybutyramide, (R)-2-[(5-chlorothiophene-2-carbonyl)amino]-N-[3-methyl-4-(3-oxomorpholin-4-yl)phenyl]-4-methoxybutyramide,
(R)-2-[(5-chlorothiophene-2-carbonyl)amino]-N-[3-fluoro-4-(3-oxomorpholin-4-yl)phenyl]-4-methylvaleramide,
(R)-2-[(5-chlorothiophene-2-carbonyl)amino]-N-[3-fluoro-4-(3-oxomorpholin-4-yl)phenyl]valeramide,
(R)-2-[(5-chlorothiophene-2-carbonyl)amino]-N-[3-chloro-4-(3-oxomorpholin-4-yl)phenyl]propionamide,
(R)-2-[(5-chlorothiophene-2-carbonyl)amino]-N-[4-(3-oxomorpholin-4-yl)phenyl]-4-(tert-butyloxycarbonyl)butyramide,
(R)-2-[(5-chlorothiophene-2-carbonyl)amino]-N-[3-methyl-4-(3-oxomorpholin-4-yl)phenyl]-4-(tert-butyloxycarbonyl)butyramide,
(R)-2-[(5-chlorothiophene-2-carbonyl)amino]-N-[4-(2-oxopiperidin-1-yl)phenyl]-4-(tert-butyloxycarbonyl)butyramide,
(R)-2-[(5-chlorothiophene-2-carbonyl)amino]-N-[4-(3-oxomorpholin-4-yl)phenyl]-4-(tert-butyloxycarbonylamino)butyramide,
(R)-2-[(5-chlorothiophene-2-carbonyl)amino]-N-[3-methyl-4-(3-oxomorpholin-4-yl)-phenyl]-4-(tert-butyloxycarbonylamino)butyramide,
(R)-2-[(5-chlorothiophene-2-carbonyl)amino]-N-[4-(3-oxomorpholin-4-yl)phenyl]-5-(tert-butyloxycarbonylamino)valeramide,
(R)-2-[(5-chlorothiophene-2-carbonyl)amino]-N-[3-methyl-4-(3-oxomorpholin-4-yl)-phenyl]-5-(tert-butyloxycarbonylamino)valeramide,
(R)-2-[(5-chlorothiophene-2-carbonyl)amino]-N-[4-(3-oxomorpholin-4-yl)-phenyl]-3-(tert-butyloxycarbonylamino)propionamide,
(R)-2-[(5-chlorothiophene-2-carbonyl)amino]-N-[3-methyl-4-(3-oxomorpholin-4-yl)-phenyl]-3-(tert-butyloxycarbonylamino)propionamide,
(R)-3-[(5-chlorothiophene-2-carbonyl)amino]-N-[3-methyl-4-(3-oxomorpholin-4-yl)-phenyl]butyramide,
(R)-3-[(5-chlorothiophene-2-carbonyl)amino]-N-[3-methyl-4-(3-oxomorpholin-4-yl)-phenyl]-5-methyladipamide,
(S)-3-[(5-chlorothiophene-2-carbonyl)amino]-N-[3-methyl-4-(3-oxomorpholin-4-yl)-phenyl]-5-methyladipamide,
(R)-2-[(5-chlorothiophene-2-carbonyl)amino]-N-[4-(2-oxo-2H-pyridin-1-yl)phenyl]-3-methoxypropionamide,
(R)-2-[(5-chlorothiophene-2-carbonyl)amino]-N-[3-methyl-4-(3-oxomorpholin-4-yl)-phenyl]-3-methoxypropionamide,
(2R,3R)-2-[(5-chlorothiophene-2-carbonyl)amino]-N-[4-(3-oxomorpholin-4-yl)phenyl]-3-methoxybutyramide,
(2R,3R)-2-[(5-chlorothiophene-2-carbonyl)amino]-N-[3-methyl-4-(3-oxomorpholin-4-yl)phenyl]-3-methoxybutyramide,
(S)-2-[(5-chlorothiophene-2-carbonyl)amino]-N-[3-methyl-4-(3-oxomorpholin-4-yl)-phenyl]-3-methoxypropionamide,
(R)-2-[(5-chlorothiophene-2-carbonyl)amino]-N-[3-trifluoromethyl-4-(3-oxomorpholin-4-yl)phenyl]-3-methoxypropionamide,
(R)-2-[(5-chlorothiophene-2-carbonyl)amino]-N-[3-chloro-4-(2-azabicyclo[2.2.2]-octan-2-yl)phenyl]-3-methoxypropionamide,
(R)-2-[(5-chlorothiophene-2-carbonyl)amino]-N-[3trifluoromethoxy-4-(2-azabicyclo-[2.2.2]octan-2-yl)phenyl]-3-methoxypropionamide,
(R)-2-[(5-chlorothiophene-2-carbonyl)amino]-N-[3-chloro-4-(3-oxomorpholin-4-yl)-phenyl]-3-methoxypropionamide,
(R)-2-[(5-chlorothiophene-2-carbonyl)amino]-N-[3-fluoro-4-(3-oxomorpholin-4-yl)-phenyl]-3-methoxypropionamide,
(R)-2-[(5-chlorothiophene-2-carbonyl)amino]-N-[3-chloro-4-(2-oxo-2H-pyridin-1-yl)-phenyl]-3-methoxypropionamide,
(R)-2-[(5-chlorothiophene-2-carbonyl)amino]-N-[3-methyl-4-(3-oxomorpholin-4-yl)-phenyl]-3-allylpropionamide,
(R)-2-[(5-chlorothiophene-2-carbonyl)amino]-N-[3-methyl-4-(3-oxomorpholin-4-yl)-phenyl]-3-propoxypropionamide,
(R)-2-[(5-chlorothiophene-2-carbonyl)amino]-N-[3-methyl-4-(3-oxomorpholin-4-yl)-phenyl]-3-ethoxypropionamide,
(R)-2-[(5-chlorothiophene-2-carbonyl)amino]-N-[3-methyl-4-(3-oxomorpholin-4-yl)-phenyl]-3-(2-methoxyethoxy)propionamide,
(2R,3R)-2-[(5-chlorothiophene-2-carbonyl)amino]-N-[3-methyl-4-(3-oxomorpholin-4-yl)phenyl]-3-ethoxybutyramide,
(2R,3R)-2-[(5-chlorothiophene-2-carbonyl)amino]-N-[3-methyl-4-(3-oxomorpholin-4-yl)phenyl]-3-(2-methoxyethoxy)butyramide,
(R)-2-[(5-chlorothiophene-2-carbonyl)amino]-N-[3-methyl-4-(3-oxomorpholin-4-yl)-phenyl]-3-methylsulfonylpropionamide,
(R)-2-[(5-chlorothiophene-2-carbonyl)amino]-N-[4-(2-oxo-2H-pyridin-1-yl)phenyl]-3-methylsulfonylpropionamide,
(R)-2-[(5-chlorothiophene-2-carbonyl)amino]-N-[4-(3-oxomorpholin-4-yl)phenyl]-3-methylsulfonylpropionamide,
(R)-2-[(5-chlorothiophene-2-carbonyl)amino]-N-[4-(3-oxomorpholin-4-yl)phenyl]-3-methylsulfonylbutyramide,
(R)-2-[(5-chlorothiophene-2-carbonyl)amino]-N-[3-methyl-4-(3-oxomorpholin-4-yl)phenyl]-3-methylsulfonylbutyramide,
(R)-2-[(5-chlorothiophene-2-carbonyl)amino]-N-[4-(2-oxo-2H-pyridin-1-yl)phenyl]-3-methylsulfonylbutyramide,
(R)-2-[(5-chlorothiophene-2-carbonyl)amino]-N-[4-(3-oxomorpholin-4-yl)phenyl]-3-carboxypropionamide,
(R)-2-[(5-chlorothiophene-2-carbonyl)amino]-N-[3-methyl-4-(3-oxomorpholin-4-yl)-phenyl]-3-carboxypropionamide,
(R)-2-[(5-chlorothiophene-2-carbonyl)amino]-N-[4-(3-oxomorpholin-4-yl)phenyl]-4-carboxybutyramide,
(R)-2-[(5-chlorothiophene-2-carbonyl)amino]-N-[3-methyl-4-(3-oxomorpholin-4-yl)-phenyl]-4-carboxybutyramide,
(R)-2-[(5-chlorothiophene-2-carbonyl)amino]-N-[4-(3-oxomorpholin-4-yl)phenyl]-4-aminobutyramide,
(R)-2-[(5-chlorothiophene-2-carbonyl)amino]-N-[3-methyl-4-(3-oxomorpholin-4-yl)-phenyl]-4-aminobutyramide,
(R)-2-[(5-chlorothiophene-2-carbonyl)amino]-N-[4-(3-oxomorpholin-4-yl)phenyl]-5-aminovaleramide, (R)-2-[(5-chlorothiophene-2-carbonyl)amino]-N-[3-methyl-4-(3-oxomorpholin-4-yl)phenyl]-5-aminovaleramide,
(R)-2-[(5-chlorothiophene-2-carbonyl)amino]-N-[4-(3-oxomorpholin-4-yl)phenyl]-3-aminopropionamide,
(R)-2-[(5-chlorothiophene-2-carbonyl)amino]-N-[3-methyl-4-(3-oxomorpholin-4-yl) phenyl]-3-aminopropionamide,
(R)-2-[(5-chlorothiophene-2-carbonyl)amino]-N-[3-methyl-4-(3-oxomorpholin-4-yl)phenyl]-3-hydroxypropionamide,
(R)-2-[(5-chlorothiophene-2-carbonyl)amino]-N-[3-4-(3-oxomorpholin-4-yl)phenyl]-3-hydroxypropionamide,
(2R,3R)-2-[(5-chlorothiophene-2-carbonyl)amino]-N-[4-(3-oxomorpholin-4-yl)phenyl]-3-hydroxybutyramide,
(2R,3R)-2-[(5-chlorothiophene-2-carbonyl)amino]-N-[4-(3-oxomorpholin-4-yl)phenyl]-3-aminocarbonyloxybutyramide,
(2R)-2-[(5-chlorothiophene-2-carbonyl)amino]-N-[3-methyl-4-(3-oxomorpholin-4-yl)phenyl]-3-aminocarbonyloxypropionamide,or
(2R,3R)-2-[(5-chlorothiophene-2-carbonyl)amino]-N-[3-methyl-4-(3-oxomorpholin-4-yl)phenyl]-3-aminocarbonyloxybutyramide,
or a pharmaceutically acceptable salt or stereoisomer thereof, or a mixture thereof.

16. A process for preparing a compound of formula I according to claim 1 or a pharmaceutically acceptable salt or stereoisomer thereof, comprising a) reacting a compound of formula II

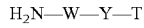   II in which
W, Y and T have the meanings indicated for the compound of formula I,
with a compound of formula III

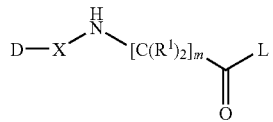   III in which
L denotes Cl, Br, I or a free or reactively functionally modified OH group, and
$R^1$, m, X and D have the meanings indicated for the compound of formula I,
or
b) reacting a compound of formula IV

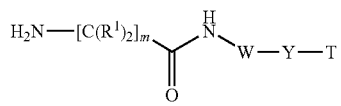   IV in which $R^1$, m, W, Y and T have the meanings indicated for the compound of formula I,
with a compound of formula V

   V in which

L denotes Cl, Br, I or a free or reactively functionally modified OH group, and
D has the meaning indicated for the compound of formula I,
and/or
a base or acid of the compound of formula I is converted into one of its salts.

17. A method for inhibiting coagulation factor Xa, comprising administering a compound of formula I according to claim 1 in an effective amount to inhibit coagulation factor Xa.

18. A method for inhibiting coagulation factor VIIa, comprising administering a compound of formula I according to claim 1 in an effective amount to inhibit coagulation factor VIIa.

19. A pharmaceutical composition comprising a compound of formula I according to claim 1 and/or a pharmaceutically acceptable salt or stereoisomer thereof, or a mixture thereof, and a pharmaceutically acceptable excipient and/or adjuvant.

20. A pharmaceutical composition according to claim 19, further comprising a pharmaceutically active ingredient other than the compound of formula I.

21. A method for treating thromboses, myocardial infarction, arteriosclerosis, angina pectoris, restenosis after angioplasty, claudicatio intermittens, or migraine, comprising administering to a subject in need thereof an effective amount of a pharmaceutical composition according to claim 19.

22. A method for treating thromboses or arteriosclerosis, comprising administering to a subject in need thereof an effective amount of a pharmaceutical composition according to claim 19.

23. A method for treating thromboses, myocardial infarction, arteriosclerosis, angina pectoris, restenosis after angioplasty, claudicatio intermittens, or migraine, comprising administering to a subject in need thereof an effective amount of a compound according to claim 15.

24. A set or kit comprising separate packs of
(a) a compound of formula I according to claim 1 and/or a pharmaceutically acceptable salt or stereoisomer thereof, or a mixture thereof, and
(b) a pharmaceutically active ingredient other than the compound of formula I.

25. A compound of formula I

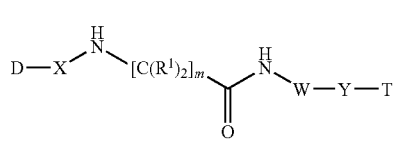   I in which
D denotes thienyl which is unsubstituted or mono- or polysubstituted by Hal, A, $OR^2$, $N(R^2)_2$, $NO_2$, CN, $COOR^2$ or $CON(R^2)_2$,
X denotes —C=O,
W denotes —$[C(R^3)_2]_n$—,
$R^1$ denotes H or A, which may be substituted by $OR^3$, $S(O)_nR^3$, $N(R^3)_2$, CN, $COOR^3$, $CON(R^3)_2$, $OCON(R^3)_2$, $N(R^3)COOR^3$, $N(R^3)CON(R^3)_2$, $N(R^3)SO_2R^3$, $SO_2N(R^3)_2$ or —C≡C—,
$R^2$ denotes H, A, —$[C(R^3)_2]_n$Ar', —$[C(R^3)_2]_n$-Het', —$[C(R^3)_2]_n$—cycloalkyl, —$[C(R^3)_2]_n$—$N(R^3)_2$ or —$[C(R^3)_2]_n$—$OR^3$,
$R^3$ denotes H or A, Y denotes Ar-diyl, T denotes a mono- or bicyclic saturated, unsaturated or aromatic carbo- or heterocycle having 0 to 4 N, O and/or S atoms which is mono- or disubstituted by =O, =S, =NR$^2$, =N—CN, =N—NO$_2$, =NOR$^2$, =NCOR$^2$, =NCOOR$^2$, and/or =NOCOR$^2$ and may furthermore be mono-, di- or trisubstituted by R$^2$, Hal, A, —[C(R$^3$)$_2$]$_n$—Ar, —[C(R$^3$)$_2$]$_n$-Het, —[C(R$^3$)$_2$]$_n$-cycloalkyl, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$NR$^2$ and/or S(O)$_n$A, A denotes unbranched or branched alkyl having 1-10 C atoms, in which one or two CH$_2$ groups may be replaced by O or S atoms and/or by —CH=CH— groups and/or 1-7 H atoms may be replaced by F, Ar denotes phenyl, naphthyl or biphenyl, each of which is unsubstituted or mono-, di- or trisubstituted by Hal, A, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^2$, SO$_2$N(R$^2$)$_2$, S(O)$_n$A, —[C(R$^3$)$_2$]$_n$—COOR$^2$ or —O—[C(R$^3$)$_2$]$_o$—COOR$^2$, Ar' denotes phenyl which is unsubstituted or mono-, di- or trisubstituted by Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$, S(O)$_n$A, —[C(R$^3$)$_2$]$_n$—COOR$^3$ or —O—[C(R$^3$)$_2$]$_o$—COOR$^3$, Het denotes a mono- or bicyclic saturated, unsaturated or aromatic heterocycle having 1 to 4 N, O and/or S atoms, which may be unsubstituted or mono-, di- or trisubstituted by carbonyl oxygen, =S, =N(R$^2$)$_2$, Hal, A, —[C(R$^3$)$_2$]$_n$—Ar, —[C(R$^3$)$_2$]$_n$-Het', —[C(R$^3$)$_2$]$_n$-cycloalkyl, —[C(R$^3$)$_2$]$_n$—OR$^2$, —[C(R$^3$)$_2$]$_n$N(R$^3$)$_2$, NO$_2$, CN, —[C(R$^3$)$_2$]$_n$—COOR$^2$, —[C(R$^3$)$_2$]$_n$—CON(R$^2$)$_2$, —[C(R$^3$)$_2$]$_n$—NR$^2$COA, NR$^2$CON(R$^2$)$_2$, —[C(R$^3$)$_2$]$_n$—NR$^2$SO$_2$A, COR$^2$, SO$_2$NR$^2$ and/or S(O)$_n$A, Het' denotes a mono- or bicyclic saturated, unsaturated or aromatic heterocycle having 1 to 4 N, O and/or S atoms, which may be unsubstituted or mono- or disubstituted by carbonyl oxygen, =S, =N(R$^3$)$_2$, Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^3$ and/or S(O)$_n$A, Hal denotes F, Cl, Br or I, m denotes 1 or 2, n denotes 0, 1 or 2, and o denotes 1, 2 or 3, or a pharmaceutically acceptable salt thereof.

\* \* \* \* \*

UNITED STATES PATENT AND TRADEMARK OFFICE
CERTIFICATE OF CORRECTION

PATENT NO.      : 7,579,346 B2                                Page 1 of 1
APPLICATION NO. : 10/535246
DATED           : August 25, 2009
INVENTOR(S)     : Dorsch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this

Fourteenth Day of September, 2010

David J. Kappos
*Director of the United States Patent and Trademark Office*